(12) United States Patent
Policker et al.

(10) Patent No.: US 7,840,269 B2
(45) Date of Patent: Nov. 23, 2010

(54) ANALYSIS OF EATING HABITS

(75) Inventors: Shai Policker, Moshav Tzur Moshe (IL); Ricardo Aviv, Haifa (IL); Ophir Biton, Zichron Yaacov (IL)

(73) Assignee: Metacure Limited, Hamilton (BM)

( * ) Notice: Subject to any disclaimer, the term of this patent is extended or adjusted under 35 U.S.C. 154(b) by 88 days.

(21) Appl. No.: 11/848,555

(22) Filed: Aug. 31, 2007

(65) Prior Publication Data
US 2007/0299320 A1 Dec. 27, 2007

Related U.S. Application Data

(63) Continuation of application No. 10/475,198, filed on Feb. 19, 2004, which is a continuation of application No. PCT/IL02/00309, filed on Apr. 16, 2002, now Pat. No. 7,330,753.

(60) Provisional application No. 60/284,497, filed on Apr. 18, 2001.

(51) Int. Cl.
*A61B 5/053* (2006.01)

(52) U.S. Cl. ............... 607/40; 607/2; 607/41; 607/45; 607/58; 607/62; 600/300; 600/546; 600/547; 600/585; 600/593

(58) Field of Classification Search ......... 607/2, 607/40–41, 45, 58, 62; 600/300, 546, 547, 600/585, 593; 128/898, 903, 920, 924, 925
See application file for complete search history.

(56) References Cited

U.S. PATENT DOCUMENTS

| | | | |
|---|---|---|---|
| 5,188,104 A | 2/1993 | Wernicke et al. |
| 5,292,344 A | 3/1994 | Douglas |
| 5,514,175 A | 5/1996 | Kim et al. |
| 5,540,730 A | 7/1996 | Terry, Jr. et al. |
| 5,792,210 A | 8/1998 | Wamubu et al. |
| 5,795,304 A | 8/1998 | Sun et al. |
| 5,891,185 A | 4/1999 | Freed et al. |
| 5,995,872 A | 11/1999 | Bourgeois |
| 6,154,676 A | 11/2000 | Levine |

(Continued)

FOREIGN PATENT DOCUMENTS

WO    WO 97/41921    11/1997

(Continued)

OTHER PUBLICATIONS

OA issued Oct. 24, 2008 in Applicant's European Patent Appln. No. EP 02 724 592.7.

(Continued)

*Primary Examiner*—Carl H Layno
*Assistant Examiner*—Deborah Malamud
(74) *Attorney, Agent, or Firm*—William H. Dippert; Eckert Seamans Cherin & Mellott, LLC

(57) ABSTRACT

Diet evaluation gastric apparatus (18) is provided, which detects when a patient (10) swallows, and detects the type and amount of matter ingested. The apparatus includes electrodes (74, 100) adapted to be coupled to the fundus and antrum of the patient and to measure electrical and mechanical activity therein, and a control unit (90) to analyze such electrical and mechanical activity and optionally apply electrical energy to modify the activity of tissue of the patient.

67 Claims, 11 Drawing Sheets

U.S. PATENT DOCUMENTS

| | | | |
|---|---|---|---|
| 6,334,073 | B1 | 12/2001 | Levine |
| 6,591,137 | B1 * | 7/2003 | Fischell et al. ............... 607/40 |
| 6,600,953 | B2 * | 7/2003 | Flesler et al. ............... 607/40 |
| 6,609,025 | B2 | 8/2003 | Barrett et al. |
| 6,735,477 | B2 | 5/2004 | Levine |
| 7,330,753 | B2 | 2/2008 | Policker et al. |
| 2004/0147816 | A1 | 7/2004 | Policker et al. |
| 2004/0162595 | A1 | 8/2004 | Foley |
| 2005/0096514 | A1 | 5/2005 | Starkebaum |
| 2006/0064037 | A1 | 3/2006 | Shalon et al. |
| 2006/0264699 | A1 | 11/2006 | Gertner |
| 2007/0027493 | A1 | 2/2007 | Ben-Haim et al. |

FOREIGN PATENT DOCUMENTS

| | | |
|---|---|---|
| WO | WO 99/00067 | 1/1999 |
| WO | WO 99/03533 | 1/1999 |
| WO | WO 00/19893 | 4/2000 |
| WO | WO 00/53257 | 9/2000 |
| WO | WO 02/82968 | 10/2002 |

OTHER PUBLICATIONS

An Office Action dated Dec. 11, 2006, which issued during the prosecution of Applicant's U.S. Appl. No. 10/475,198.

An Office Action dated May 16, 2007, which issued during the prosecution of Applicant's U.S. Appl. No. 10/250,714.

An Office Action dated Oct. 6, 2006, which issued during the prosecution of Applicant's U.S. Appl. No. 10/250,714.

An Office Action dated Feb. 7, 2006, which issued during the prosecution of Applicant's U.S. Appl. No. 10/250,714.

A Partial European Search Report dated Feb. 20, 2009, which issued during the prosecution of Applicant's European Patent Application No. EP 02 72 7012.

An Office Action dated Apr. 21, 2008, which issued during the prosecution of Applicant's Japanese Patent Application No. 2002-554044.

An Office Action dated Jun. 10, 2008, which issued during the prosecution of Applicant's Japanese Patent Application No. 2002-580780.

An International Search Report and A Written Opinion, both dated Oct. 28, 2008, issued during the prosecution of Applicant's PCT/IL08/00646.

An Office Action dated Nov. 12, 2005, which issued during the prosecution of Applicant's Chinese Patent Application No. 02806011.3.

An Office Action dated Apr. 17, 2006, which issued during the prosecution of Applicant's Chinese Patent Application No. 02806011.3.

* cited by examiner

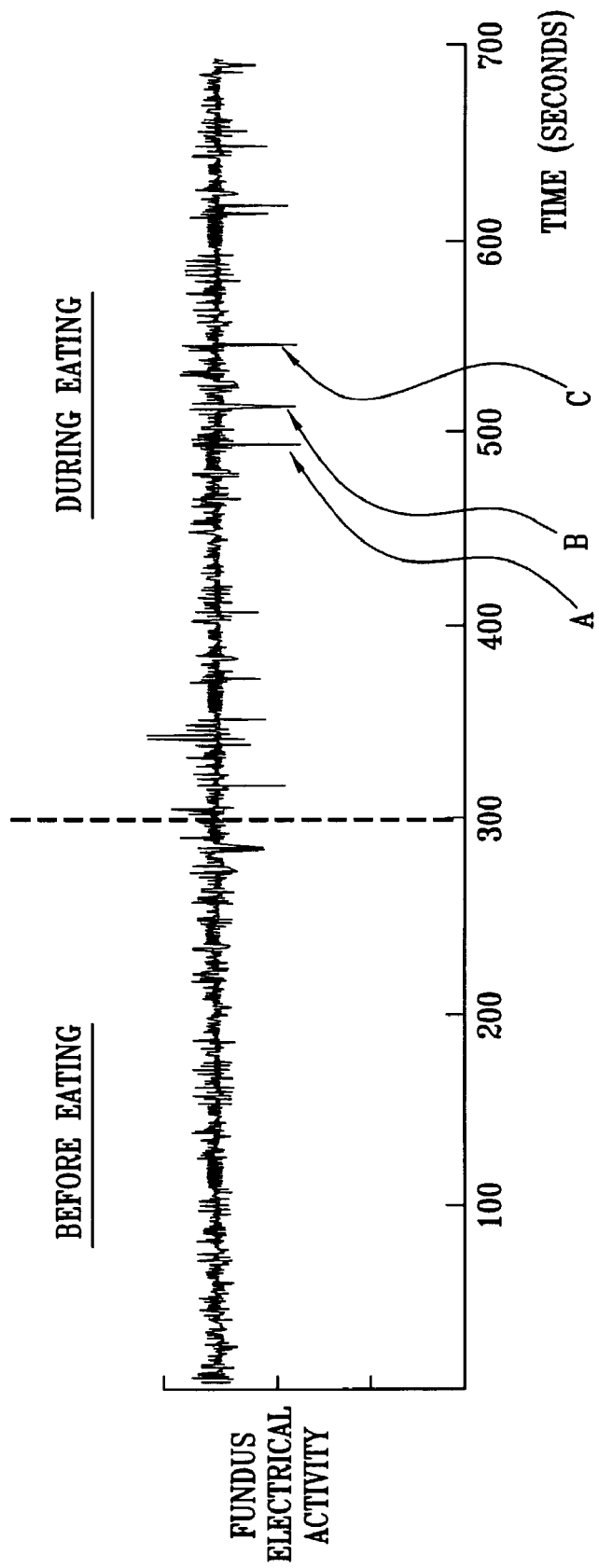

ANALYSIS OF EATING HABITS

CROSS-REFERENCE TO RELATED APPLICATIONS

The present application is a continuation of, commonly assigned U.S. patent application Ser. No. 10/475,198, filed Feb. 19, 2004, which issued as U.S. Pat. No. 7,330,753, which is a National Phase application of PCT Application No. PCT/IL02/00309, filed Apr. 16, 2002, which claims priority from U.S. provisional patent application Ser. No. 60/284,497, filed Apr. 18, 2001.

FIELD OF THE INVENTION

The present invention relates generally to tracking eating habits, and specifically to invasive techniques and apparatus for detecting and analyzing the swallowing and digesting of food.

BACKGROUND OF THE INVENTION

Morbid obesity is a difficult to treat chronic condition defined by a body mass index (BMI=mass/height$^2$ [kg/m$^2$]) greater than 40. For obese persons, excessive weight is commonly associated with increased risk of cardiovascular disease, diabetes, degenerative arthritis, endocrine and pulmonary abnormalities, gallbladder disease and hypertension. Additionally, such persons are highly likely to experience psychological difficulties because of lifestyle restrictions such as reduced mobility and physical capacity, due to back pain, joint problems, and shortness of breath. In severe cases, this can contribute to absenteeism and unemployment. Moreover, impairment of body image can lead to significant psychological disturbances. Repeated failures of dieting and exercise to resolve the problem of obesity can result in feelings of despair and the development of clinical depression.

Bariatric surgery is often recommended for persons suffering from morbid obesity. Preferably, the invasive treatment is accompanied by changes in lifestyle, such as improved regulation of eating habits and an appropriate exercise regimen. Such lifestyle changes are dependent upon the self-discipline and cooperation of the patient.

A book entitled, *Textbook of Gastroenterology*, 3rd edition, edited by Yamada (Lippincott, Williams & Wilkins), which is incorporated herein by reference, has in Chapter 10 thereof a description of the physiology of gastric motility and gastric emptying.

An abstract entitled, "Gastric myoelectrical pacing as therapy for morbid obesity: Preliminary results," by Cigaina et al., retrieved on Dec. 24, 2000 from the Web-site http://www.med-online.com/transneuronix/Product/abstract.htm, which is incorporated herein by reference, describes a method for applying monopolar and bipolar gastric stimulation to achieve weight loss.

An abstract entitled, "Implantable gastric stimulator (IGS) as therapy for morbid obesity: Equipment, surgical technique and stimulation parameters," by Cigaina et al., retrieved on Dec. 24, 2000 from the Web-site http://www.med-online.com/transneuronix/Product/abstract.htm, which is incorporated herein by reference, describes techniques of electrical signal therapy designed to treat obesity.

US Patent 6,129,685 to Howard, which is incorporated herein by reference, describes apparatus and methods for regulating appetite by electrical stimulation of the hypothalamus and by microinfusion of an appropriate quantity of a suitable drug to a distinct site or region within the hypothalamus.

U.S. Pat. No. 4,823,808 to Clegg et al., which is incorporated herein by reference, describes a method for treating obesity, including receiving a physiological measurement and generating audio or visual feedback for the patient to hear or see. The feedback is used for purposes of teaching behavior modification.

U.S. Pat. No. 5,868,141 to Ellias, which is incorporated herein by reference, describes an endoscopic stomach insert for reducing a patient's desire to eat.

U.S. Pat. No. 6,067,991 to Forsell, U.S. Pat. No. 5,601,604 to Vincent, U.S. Pat. No. 5,234,454 to Bangs, U.S. Pat. No. 4,133,315 to Berman et al., U.S. Pat. No. 4,416,267 to Garren et al., and U.S. Pat. Nos. 4,592,339, 5,449,368, 5,226,429 and 5,074,868 to Kuzmak, which are incorporated herein by reference, describe mechanical instruments for implantation in or around the stomach of an obese patient.

U.S. Pat. No. 5,690,691 to Chen et al., which is incorporated herein by reference, describes a gastric pacemaker for treating obesity and other disorders. The pacemaker includes multiple electrodes which are placed at various positions on the gastrointestinal (GI) tract, and deliver phased electrical stimulation to pace peristaltic movement of material through the GI tract.

U.S. Pat. No. 5,423,872 to Cigaina, which is incorporated herein by reference, describes apparatus for applying electrical pulses to the distal gastric antrum of a patient, so as to reduce the motility of the stomach and to thereby treat obesity or another disorder.

U.S. Pat. Nos. 5,188,104 and 5,263,480 to Wernicke et al., which are incorporated herein by reference, describe a method for stimulating the vagus nerve of a patient so as to alleviate an eating disorder.

U.S. Pat. Nos. 6,104,955, 6,091,992, and 5,836,994 to Bourgeois, U.S. Pat. No. 6,026,326 to Bardy, and U.S. Pat. No. 3,411,507 to Wingrove, which are incorporated herein by reference, describe the application of electrical signals to the GI tract to treat various physiological disorders.

U.S. Pat. No. 5,979,449 to Steer, which is incorporated herein by reference, describes an oral appliance for appetite suppression.

U.S. Pat. No. 4,975,682 to Kerr et al., which is incorporated herein by reference, describes apparatus for food intake regulation which is external to the body and which is based upon the voluntary cooperation of the subject in order to be effective.

U.S. Pat. No. 5,861,014 to Familoni, U.S. Pat. No. 5,716,385 to Mittal et al., and U.S. Pat. No. 5,995,872 to Bourgeois, are incorporated herein by reference, and describe methods and apparatus for stimulation of tissue, particularly gastrointestinal tract tissue.

PCT Patent Publication WO 98/10830 to Ben-Haim et al., entitled, "Fencing of cardiac muscles," and U.S. patent application Ser. No. 09/254,903 in the national phase thereof, both of which are assigned to the assignee of the present patent application and are incorporated herein by reference, describe various methods for controlling the behavior of muscle tissue, for example by blocking or altering the transmission of signals therethrough.

PCT Patent Publication WO 99/03533 to Ben-Haim et al., entitled, "Smooth muscle controller," and U.S. patent application Ser. No. 09/481,253 in the national phase thereof, both of which are assigned to the assignee of the present patent application and are incorporated herein by reference, describe apparatus and methods for applying signals to smooth muscle so as to modify the behavior thereof. In particular, apparatus for controlling the stomach is described in which a controller applies an electrical field to electrodes on the stomach wall so as to modify the reaction of muscle tissue therein to an activation signal, while not generating a propagating action potential in the tissue. In the context of the present patent application and in the claims, the use of such a non-excitatory signal to modify the response of one or more cells to electrical activation thereof, without inducing action potentials in the cells, is referred to as Excitable-Tissue Control (ETC). Use of an ETC signal is described in the PCT Patent Publication with respect to treating obesity, by applying the ETC signal to the stomach so as to delay or prevent emptying of the stomach. In addition, a method is described for increasing the motility of the gastrointestinal tract, by applying an ETC signal to a portion of the tract in order to increase the contraction force generated in the portion.

SUMMARY OF THE INVENTION

It is an object of some aspects of the present invention to provide apparatus and methods for detecting and tracking the swallowing of solids and liquids.

It is a further object of some aspects of the present invention to provide apparatus and methods for detecting, tracking, quantifying and determining the qualitative character of ingested liquids and solids.

It is still a further object of some aspects of the present invention to provide improved apparatus and methods for treating obesity.

It is yet a further object of some aspects of the present invention to provide apparatus and methods that enable the implementation of changes in food ingestion habits in a predictable and controlled manner.

It is an additional object of some aspects of the present invention to provide methods and apparatus for regulating food ingestion.

It is still an additional object of some aspects of the present invention to provide apparatus and methods for bariatric surgery that are less drastic than those currently employed.

In preferred embodiments of the present invention, apparatus for detecting, tracking, quantifying and determining the qualitative character of ingested liquids and solids comprises a sensor coupled to a patient's gastrointestinal tract. Preferably, the sensor generates a signal indicative of the swallowing of food. An analysis module preferably determines a quality of the food, for example, whether it is predominantly solid or liquid, and stores this information in an electronic memory. Alternatively or additionally, the analysis module determines other characteristics of the ingested material, for example, the nutritional, chemical, and/or caloric content. "Food," as used in the context of the present patent application and in the claims, is to be understood as including both solid and liquid food. "Swallowing," as used in the context of the present patent application and in the claims, is to be understood as being indicative of the onset of eating.

In some preferred embodiments of the present invention, swallowing is detected by tracking the electrical activity in muscle tissue in the fundic region of the stomach. Typically, the commencement of enhanced electrical activity is also detected in muscle tissue in the antral region of the stomach. Measurement of the time delay between swallowing and the commencement of electrical activity in the antrum is preferably used to differentiate between solid and liquid matter, which are generally passed at different rates through the stomach.

Alternatively or additionally, swallowing is detected by at least one sensor placed at a site on the gastrointestinal tract other than the fundic region of the stomach, and the sensor generates a signal indicative of swallowing. Appropriate sites include, but are not limited to, a site on the esophagus, a site on the stomach, and a site on the throat. Whenever detection of swallowing is described in the present patent application with respect to fundic activity, it is to be understood as being by way of example, and not as excluding detection by a sensor located elsewhere on the gastrointestinal tract.

Preferably, measurement of the intensity and/or duration of the electrical activity in the antral region is correlated with aspects of fundic electrical activity denoting swallowing, as described hereinbelow, such that ingested matter of differing chemical and nutritional content can be distinguished. Further preferably, the amount of food accumulated in the fundus or antrum is estimated by measuring a level of electrical activity at various sites in the stomach.

Typically, electrical activity response criteria of the stomach of an individual patient are determined and calibrated by measuring the response of the patient's stomach to various types of solid and liquid food. To ensure appropriate compliance, calibration is preferably performed under the supervision of a healthcare worker. For illustration, a table such as the following may be established for a particular patient. Except with respect to the example of sugarless chewing gum, these illustrative values are shown with respect to a constant volume of food or liquid ingested (e.g., 100 ml or steak, water, or tomato juice).

TABLE I

| Substance | Fundic activity level | Antral activity level | Time delay until onset of antral activity |
|---|---|---|---|
| Sugarless chewing gum | 1 | 1 | — |
| Non-caloric liquid - Water | 2 | 1 | — |
| Caloric liquid - Tomato juice | 2 | 2 | <1 Minute |
| Caloric liquid - Milk | 2 | 2 | <1 Minute |
| Solid - Apple | 2 | 2 | Minutes |
| Solid - Meat | 2 | 3 | Minutes |

In this illustration, the measured data are preferably analyzed to determine signal characteristics which correspond to the indicated fundic and antral electrical 5 activity levels. For example, calibration of fundic activity during the chewing of sugarless gum typically yields a low level indication of swallowing, while calibration during the swallowing of liquids and solids yields a greater fundic response. Similarly, there is typically no significant antral response to the patient drinking water, while calibration during the digestion of liquids and solids having higher caloric content yields a greater antral response. Measurements are preferably made of the delay time between swallowing and the commencement of antral activity, because consumption of liquids is typically characterized by a rapid transition from the fundus to the antrum, while solids typically stay in the fundus for at least about 10 minutes prior to being passed to the antrum. Preferably, a large variety of liquids and solids are used to establish a profile of electrical response characteristics for each patient.

For some applications, various supplemental sensors are also applied to the gastrointestinal tract or elsewhere on or in the patient's body. These supplemental sensors, which may comprise pH sensors, blood sugar sensors, ultrasound transducers or mechanical sensors, typically convey signals to a control unit of the apparatus indicative of a characteristic of solids or liquids ingested by the patient. For example, an ultrasound transducer may be coupled to indicate whether ingesta are solid or liquid, and a pH sensor may indicate that an acidic drink such as tomato juice was consumed rather than a more basic liquid such as milk.

In a preferred embodiment, the collected data are stored and intermittently uploaded to an external computer, preferably by a wireless communications link, for review by the patient's physician, to enable monitoring of the patient's adherence to a dietary regimen.

For some applications, a specific schedule of allowed food ingestion is pre-programmed by the physician into the memory, and a processor is continuously operative to detect whether food consumption is taking place in accordance with the programmed schedule. For some patients, the schedule may be less strict with respect to drinking certain types of liquids, and more strict with respect to eating certain types of solid food. When an exception from the schedule is detected, the processor preferably actuates a signal generator to convey an ingestion-control signal to the patient, in order to encourage the patient to adhere to the schedule. Preferably, but not necessarily, apparatus and methods described in U.S. Provisional Patent Application No. 60/259,925, entitled, "Regulation of eating habits," filed Jan. 5, 2001, and in a PCT patent application entitled, "Regulation of eating habits," filed in January, 2002, both of which are assigned to the assignee of the present patent application and incorporated herein by reference, are utilized in the administration of the ingestion-control signal. Alternatively or additionally, the signal generator generates a visual, audio, or other cue or causes another reasonable discomfort to encourage the patient to adhere to the schedule.

For embodiments in which this form of dietary monitoring is supplemented by dietary regulation, the apparatus preferably compares the indications of actual food and drink consumption with the pre-programmed schedule. In the event of a sufficient level of patient non-compliance, the ingestion-control signal is preferably delivered to the patient's stomach via a set of electrodes placed in a vicinity thereof, so as to induce a sensation of discomfort or minor nausea. For example, an unpleasant sensation such as nausea may be induced by altering the natural electrical activity of the stomach, thereby inducing gastric dysrhythmia, or, alternatively, discomfort may be induced by pacing the rectus abdominus muscle.

Alternatively or additionally, the signal is applied to another site on or in the patient's body. For example, the ingestion-control signal may be applied mechanically or electrically in a vicinity of the cochlear nerve, so as to induce vertigo. Alternatively, the signal is applied so as to generate a brief pain sensation anywhere on the patient's body, which only recurs if the patient continues to eat. Further alternatively, the signal is applied to the esophagus or to the lower esophageal sphincter, so as to cause contraction of muscle tissue therein, thereby making any further eating difficult or very uncomfortable.

Alternatively or additionally, the ingestion-control signal is configured so as to induce a feeling of satiation, preferably but not necessarily in accordance with methods described in U.S. patent application Ser. No. 09/734,358, entitled, "Acute and chronic electrical signal therapy for obesity," filed on Dec. 21, 2000, which is assigned to the assignee of the present patent application and is incorporated herein by reference. For example, methods described in that application for engendering a feeling of satiation may be applied in conjunction with embodiments of the present invention, such that muscles in the vicinity of stretch receptors in the stomach are caused to contract, thereby resulting in decreased hunger sensations. Alternatively or additionally, the feeling of satiation is induced by applying electrical signals which enhance the mobility of chyme from the fundus to the antrum of the stomach, where stretch-receptor signals are generally generated to a greater extent for a given quantity of food than in the fundus.

In a preferred embodiment, when an exception from the schedule of allowed food ingestion is detected, the processor preferably conveys the exception to an external operator control unit, which in turn wirelessly communicates the exception in real time to a remote computer system. The remote computer system can be configured to analyze the exception based on predetermined rules and, if necessary, perform an appropriate action, such as notification of a healthcare worker, care provider, or family member of the patient, in order to encourage the patient to adhere to the schedule.

Preferably, the schedule of allowed food ingestion can be modified after implantation of the apparatus, typically by means of a wireless communications link. In this manner, the schedule can be adjusted in response to changes in the patient's eating habits and experience with the apparatus.

There is therefore provided, in accordance with a preferred embodiment of the present invention, gastric apparatus, including:

a gastrointestinal sensor, adapted to be coupled to a gastrointestinal site of a subject and to generate a gastrointestinal sensor signal responsive to a property of the gastrointestinal site;

a set of one or more antral sensors, adapted to be coupled to an antral site of an antrum of the stomach and to generate an antral sensor signal responsive to a property of the antrum; and a control unit, adapted to receive and analyze the gastrointestinal and antral sensor signals, and to determine, responsive thereto, a characteristic of a food ingested by the subject.

Preferably, the control unit is adapted to be implanted in the subject.

In a preferred embodiment, the characteristic of the ingested food includes a caloric content of the ingested food, and the control unit is adapted to determine the caloric content. Alternatively or additionally, the characteristic of the ingested food includes a chemical content of the ingested food, and the control unit is adapted to determine the chemical content. Further alternatively or additionally, the characteristic of the ingested food includes a nutritional content of the ingested food, and the control unit is adapted to determine the nutritional content.

For some applications, the apparatus includes an operator unit, which is adapted to be disposed external to the subject and to transmit a control signal to the control unit.

In a preferred embodiment, the gastrointestinal sensor is adapted to generate a swallowing sensor signal responsive to swallowing by the subject. Typically, the gastrointestinal sensor is adapted to be placed at an esophageal site of the subject, a site of the stomach of the subject, and/or a site of a throat of the subject.

Preferably, the gastrointestinal sensor includes a set of one or more fundic sensors, adapted to be coupled to a fundic site of a fundus of the stomach of the subject and to generate a fundic sensor signal responsive to a property of the fundus, and the control unit is adapted to receive and analyze the fundic and antral sensor signals, and to determine, responsive thereto, the characteristic of the ingested food. In a preferred embodiment, the fundic sensor set includes one or more strain gauges. Alternatively or additionally, the antral sensor set includes one or more strain gauges.

Typically, the fundic sensor set includes a set of fundic electrodes, adapted to generate a fundic electrode signal responsive to a property of the fundus, the antral sensor set includes a set of antral electrodes, adapted to generate an antral electrode signal responsive to a property of the antrum, and the control unit is adapted to receive and analyze the fundic and antral electrode signals, and to determine, responsive thereto, the characteristic of the ingested food. For example, the control unit may be adapted to determine, responsive to an analysis of at least one of the electrode signals, an amount of the ingested food accumulated in a region of the stomach. Alternatively or additionally, the control unit is adapted to count, responsive to an analysis of at least one of the electrode signals, a number of meals ingested by the subject during a period of time.

The antral electrode set typically includes two antral electrodes, adapted to be coupled to two sites of the antrum, and the control unit is adapted to identify a measure of electrical impedance between the two sites of the antrum. In this case, the control unit is preferably adapted to determine the characteristic of the ingested food, responsive to a change in the measure of electrical impedance. For some applications, the fundic electrode set includes two fundic electrodes, adapted to be coupled to two sites of the fundus, and the control unit is adapted to identify a measure of electrical impedance between the two sites of the fundus. For example, the control unit may be adapted to determine the characteristic of the ingested food, responsive to a change in the measure of electrical impedance. Alternatively or additionally, the control unit is adapted to identify an increased measure of electrical impedance relative to a baseline value as indicative of eating. Further alternatively or additionally, the control unit is adapted to identify a substantial return towards a baseline value of the measure of electrical impedance as indicative of a termination of eating.

For some applications, the control unit is adapted to identify an increase in the measure of electrical impedance as indicative of an onset of eating. For example, the control unit may be adapted to detect the onset of eating, responsive to the increase in the measure of electrical impedance being greater than 5 ohms per centimeter of distance between the two sites of the fundus.

In a preferred embodiment, the control unit is adapted to perform a calibration including measurement of a response of the fundic and antral electrode signals to ingestion by the subject of one or more test foods. For example, the one or more foods may include one or more solid foods, and the control unit may be adapted to perform the calibration responsive to ingestion of the one or more solid foods. Alternatively or additionally, the one or more foods includes one or more liquid foods, and the control unit is adapted to perform the calibration responsive to ingestion of the one or more liquid foods. Further alternatively or additionally, the one or more foods includes one or more solid foods and one or more liquid foods, and herein the control unit is adapted to perform the calibration responsive to ingestion of the one or more solid foods and the one or more liquid foods.

In a preferred embodiment, the antral electrode set is adapted to generate the antral electrode signal responsive to an electrical potential change generated responsive to a contraction of a muscle of the antrum. In this case, the control unit is preferably adapted to determine, responsive to an amplitude of the antral electrode signal, the characteristic of the ingested food. Alternatively or additionally, the control unit is adapted to determine, responsive to a frequency of the antral electrode signal, the characteristic of the ingested food. Further alternatively or additionally, the control unit is adapted to determine, responsive to a spike energy per antral cycle of electrical activity, the characteristic of the ingested food. Still further alternatively or additionally, the control unit is adapted to determine, responsive to a duration of the antral electrode signal, the characteristic of the ingested food.

In a preferred embodiment, the control unit is adapted to determine, responsive to a change in a rate of antral electrode signal events, the characteristic of the ingested food. The control unit may alternatively or additionally be adapted to identify an increase in an amplitude of the antral electrode signal as indicative of an onset of a cephalic phase occurring in the subject. For some applications, the control unit is adapted to identify an increase in an amplitude of the antral electrode signal as indicative of an onset of antral digestion. Alternatively or additionally, the control unit is adapted to identify a reduction in a rate of antral electrode signal events as indicative of an onset of antral digestion.

For some applications, the control unit is adapted to identify an increased amplitude of the antral electrode signal relative to a baseline value as indicative of antral digestion. Alternatively or additionally, the control unit is adapted to identify a reduced rate of antral electrode signal events relative to a baseline value as indicative of antral digestion. Further alternatively or additionally, the control unit is adapted to identify a substantial return towards a baseline value of an amplitude of the antral electrode signal as indicative of a termination of antral digestion. Still further alternatively or additionally, the control unit is adapted to identify a substantial return towards a baseline value of a rate of antral electrode signal events as indicative of a termination of antral digestion.

The control unit is preferably adapted to determine the characteristic of the ingested food, responsive to a time delay between an onset of eating and an onset of a decreased rate of electrical events in the antrum. For some applications, the control unit is adapted to determine the characteristic of the ingested food, responsive to the time delay and responsive to a threshold time delay. Alternatively or additionally, the control unit is adapted to determine, responsive to the time delay, an extent to which the ingested food includes solid food matter. In this case, the control unit is preferably adapted to determine that the ingested food includes solid food matter, responsive to the time delay being more than about one minute. For some applications, the control unit is adapted to determine that the ingested food includes predominantly solid food matter, responsive to the time delay being more than about 5 minutes.

In a preferred embodiment, the control unit is adapted to determine, responsive to the time delay, an extent to which the ingested food includes liquid food matter. For example, the control unit may be adapted to determine that the ingested food includes liquid food matter, responsive to the time delay being less than about 5 minutes. Alternatively or additionally, the control unit is adapted to determine that the ingested food includes predominantly liquid food matter, responsive to the time delay being less than about one minute.

For some applications, the control unit is adapted to determine the characteristic of the ingested food, responsive to a time delay between an onset of eating and an onset of increased electrical activity in the antrum. In this case, the control unit is preferably adapted to determine the characteristic of the ingested food, responsive to the time delay and responsive to a threshold time delay. Further preferably, the control unit is adapted to determine, responsive to the time delay, an extent to which the ingested food includes solid food matter. For example, the control unit may be adapted to determine that the ingested food includes solid food matter, responsive to the time delay being more than about one minute. Alternatively or additionally, the control unit may be adapted to determine that the ingested food includes predominantly solid food matter, responsive to the time delay being more than about 5 minutes. In a preferred embodiment, the control unit is adapted to determine, responsive to the time delay, an extent to which the ingested food includes liquid food matter. For example, the control unit may be adapted to determine that the ingested food includes liquid food matter, responsive to the time delay being less than about 5 minutes. Alternatively or additionally, the control unit is adapted to determine that the ingested food includes predominantly liquid food matter, responsive to the time delay being less than about one minute.

Preferably, the fundic electrode set is adapted to generate the fundic electrode signal responsive to an electrical potential change generated responsive to a contraction of a muscle of the fundus. For example, the control unit may be adapted to determine the characteristic of the ingested food responsive to an amplitude of the fundic electrode signal, a frequency of the fundic electrode signal, a duration of the fundic electrode signal, and/or a change in a rate of fundic electrode signal events of the fundic electrode signal.

In a preferred embodiment, the control unit is adapted to identify an increased amplitude of the fundic electrode signal relative to a baseline value as indicative of eating. Alternatively or additionally, the control unit is adapted to identify an increased frequency of the fundic electrode signal relative to a baseline value as indicative of eating. Further alternatively or additionally, the control unit is adapted to identify a substantial return towards a baseline value of an amplitude of the fundic electrode signal as indicative of a termination of eating. Still further alternatively or additionally, the control unit is adapted to identify a substantial return towards a baseline value of a frequency of the fundic electrode signal as indicative of a termination of eating. For some applications, the control unit is adapted to identify an increase in an amplitude of the fundic electrode signal as indicative of an onset of eating. For example, the control unit may be adapted to detect the onset of eating responsive to the increase in the amplitude of the fundic electrode signal being greater than about 20 percent.

In a preferred embodiment, the control unit is adapted to identify an increase in a frequency of the fundic electrode signal as indicative of an onset of eating. For example, the control unit may be adapted to detect the onset of eating, responsive to the increase in the frequency being greater than about 10 percent.

In a preferred embodiment, the control unit includes a memory, adapted to store a result of the analysis performed by the control unit. Preferably, the memory is adapted to upload the stored result to an external computer, e.g., by using a wireless communications link.

In a preferred embodiment, the apparatus includes a supplemental sensor adapted to be placed at a site of the subject and to convey a supplemental sensor signal to the control unit. The control unit is preferably adapted to receive and analyze the supplemental sensor signal, and to determine, responsive thereto, the characteristic of the ingested food. Alternatively or additionally, the control unit is adapted to receive and analyze the supplemental sensor signal, and to determine, responsive thereto, an onset of eating by the subject. Further alternatively or additionally, the control unit is adapted to receive and analyze the supplemental sensor signal, and to determine, responsive thereto, eating by the subject. Still further alternatively or additionally, the control unit is adapted to receive and analyze the supplemental sensor signal, and to determine, responsive thereto, a termination of eating by the subject. Preferably, the supplemental sensor includes an electrode, a pH sensor, a blood sugar sensor, an ultrasound transducer, and/or a mechanical sensor in a preferred embodiment, the supplemental sensor is adapted to be placed at a gastrointestinal site of the subject, an esophageal site of the subject, a site of the stomach of the subject, and/or a site of a throat of the subject.

For some applications, the control unit includes a memory, adapted to store a schedule of allowed food ingestion, wherein the apparatus includes an operator unit, which is adapted to be disposed external to the subject, and wherein the operator unit is adapted to generate an external cue when the analysis performed by the control unit is indicative of the subject not eating in accordance with the ingestion schedule. For example, the external cue may include a visual cue, and the operator unit is adapted to generate the visual cue. Alternatively or additionally, the external cue includes an audio cue, and the operator unit is adapted to generate the audio cue. For some applications, the operator unit includes a user override, adapted to be used by the subject and adapted to disable the cue. Alternatively or additionally, the operator unit is adapted to modify the schedule stored in the memory. For example, the operator unit may be adapted to modify the schedule responsive to information obtained by the operator unit, e.g., via a wireless communications link.

In a preferred embodiment, the apparatus includes a set of one or more current-application electrodes, adapted to be coupled to a tissue of the subject, and wherein the control unit is adapted to drive a current, responsive to the analysis, through the set of current-application electrodes into the tissue. For example, the current-application electrode set may be adapted to be placed at an aural site of the subject, at an esophageal site of the subject, and/or at a site of the stomach of the subject. For some applications, the control unit is adapted to drive the current into the tissue responsive to the characteristic of the ingested food. In a preferred embodiment, the control unit is adapted to apply a pacing signal to a rectus abdominus muscle of the subject. For some applications, the control unit is adapted to drive the current into the tissue responsive to a time of the subject eating.

In a preferred embodiment, the control unit is adapted to configure the current such that driving the current induces gastric dysrhythmia. Alternatively or additionally, the control unit is adapted to configure the current such that driving the current disrupts coupling of gastric mechanical activity and gastric electrical activity of the subject. Further alternatively or additionally, the control unit is adapted to configure the current such that driving the current induces a sensation of discomfort in the subject. Still further alternatively or additionally, the control unit is adapted to configure the current such that driving the current induces a sensation of nausea in the subject. Yet further alternatively or additionally, the control unit is adapted to configure the current such that driving the current induces a sensation of vertigo in the subject.

In a preferred embodiment, the control unit is adapted to drive the current-application electrode set to apply an Excitable-Tissue Control (ETC) signal to the tissue. For example, the control unit may be adapted to drive the current-application electrode set to apply a stimulatory pulse at a site of application of the ETC signal. Alternatively or additionally, the control unit is adapted to drive the current-application electrode set to apply a stimulatory pulse to tissue at a site other than a site of application of the ETC signal. Still further alternatively or additionally, the control unit is adapted to drive the current-application electrode set to apply the ETC signal in order to increase an aspect of contraction of the tissue. For some applications, the control unit is adapted to drive the current-application electrode set to apply the ETC signal in order to cause tissue contraction in a first portion of the stomach of the subject, and stretching of a stretch receptor of the stomach in a second portion of the stomach. Alternatively or additionally, the control unit is adapted to drive the current-application electrode set to apply the ETC signal in order to increase a contraction strength of tissue in a vicinity of a stretch receptor of the stomach of the subject, so as to increase a sensation of satiation of the subject. Further alternatively or additionally, the control unit is adapted to drive the current-application electrode set to apply the ETC signal to the tissue so as to enhance movement of chyme from a fundus to the antrum of the stomach of the subject.

In a preferred embodiment, the control unit includes a memory, adapted to store a schedule of allowed food ingestion, and wherein the control unit is adapted to withhold driving the current when the analysis performed by the control unit is indicative of the subject eating in accordance with the ingestion schedule. Preferably, the ingestion schedule includes types of foods and associated amounts permitted during a time period, and the control unit is adapted to withhold driving the current when the analysis is indicative of the subject eating in accordance with the ingestion schedule. Alternatively or additionally, the ingestion schedule includes a number of meals permitted during a time period, and the control is adapted to withhold driving the current when the analysis is indicative of the subject eating in accordance with the ingestion schedule. Further alternatively or additionally, the ingestion schedule includes an amount of food permitted at a certain meal, and the control is adapted to withhold driving the current when the analysis is indicative of the subject eating in accordance with the ingestion schedule.

Preferably, the memory is adapted to download a new schedule from an external computer. For some applications, the apparatus includes an operator unit, which is adapted to be disposed external to the subject and to transmit a control signal to the control unit. Further preferably, the operator unit includes a user override, adapted to be used by the subject and adapted to withhold driving the current.

There is further provided, in accordance with a preferred embodiment of the present invention, a method for analyzing gastric function of a stomach of a subject, including:

sensing a property of a gastrointestinal tract of the stomach;

sensing a property of an antrum of the stomach;

analyzing the property of the gastrointestinal tract and the property of the antrum; and determining, responsive to the analysis, a characteristic of a food ingested by the subject.

The present invention will be more fully understood from the following detailed description of the preferred embodiments thereof, taken together with the drawings, in which:

BRIEF DESCRIPTION OF THE DRAWINGS

FIG. 4 is a graph showing electrical activity in the fundus of a normal rabbit before and during eating, and results of analysis thereof, in accordance with a preferred embodiment of the present invention;

DETAILED DESCRIPTION OF PREFERRED EMBODIMENTS

Figure 1:
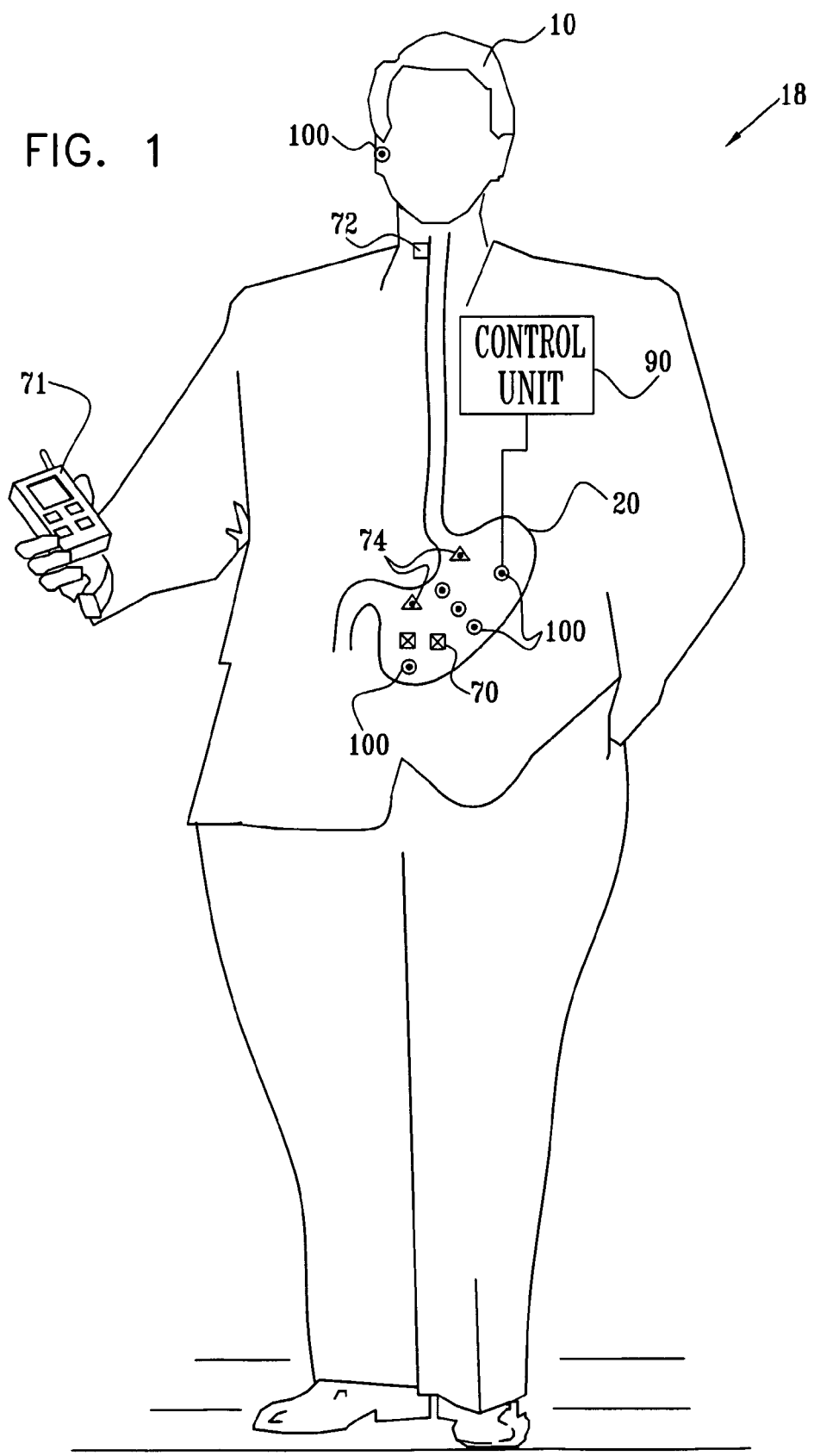
FIG. 1 is a schematic illustration of apparatus for treating obesity, in accordance with a preferred embodiment of the present invention.

FIG. 1 is a schematic illustration of diet evaluation apparatus 18, which detects when a patient 10 swallows, and detects the type and amount of matter ingested, in accordance with a preferred embodiment of the present invention. Preferably, but not necessarily, apparatus 18 additionally determines, responsive to the detection, whether to apply electrical energy to modify the activity of tissue of patient 10. Apparatus 18 typically comprises mechanical sensors 70, supplemental sensors 72, local sense electrodes 74, operator controls 71, and one or more current-application electrodes 100.

Electrodes 74 and 100 are typically coupled to the serosal layer of a stomach 20 and/or inserted into the muscular layer of the stomach in the fundic and antral regions. Alternatively or additionally, the electrodes are coupled elsewhere on the stomach, gastrointestinal tract, or to other suitable locations in or on the patient's body. The number of electrodes and sensors, as well as the positions thereof, are shown in FIG. 1 by way of example, and other sites on stomach 20 or in or on the patient's body are appropriate for electrode and sensor placement in other applications of the present invention. Different types of electrodes known in the art are typically selected based on the specific condition of the patient's disorder, and may comprise stitch, coil, screw, patch, basket, needle and/or wire electrodes, or substantially any other electrode known in the art of electrical stimulation or sensing in tissue.

Preferably, apparatus 18 is implanted in patient 10 in a manner generally similar to that used to implant gastric pacemakers or other apparatus for stimulating or sensing in the gastrointestinal tract that are known in the art. As appropriate, techniques described in one or more of the references cited in the Background section of the present patent application may be adapted for use with these embodiments of the present invention. Other methods and apparatus useful in carrying out some embodiments of the present invention are described in the above-cited U.S. Provisional Patent Application No.

60/259,925, entitled, "Regulation of eating habits," filed on Jan. 5, 2001, and in the above-cited PCT patent application and in the above-cited U.S. patent application Ser. No. 09/734,358, entitled, "Acute and chronic electrical signal therapy for obesity," filed on Dec. 11, 2000, which are assigned to the assignee of the present patent application and are incorporated herein by reference.

Figure 2:
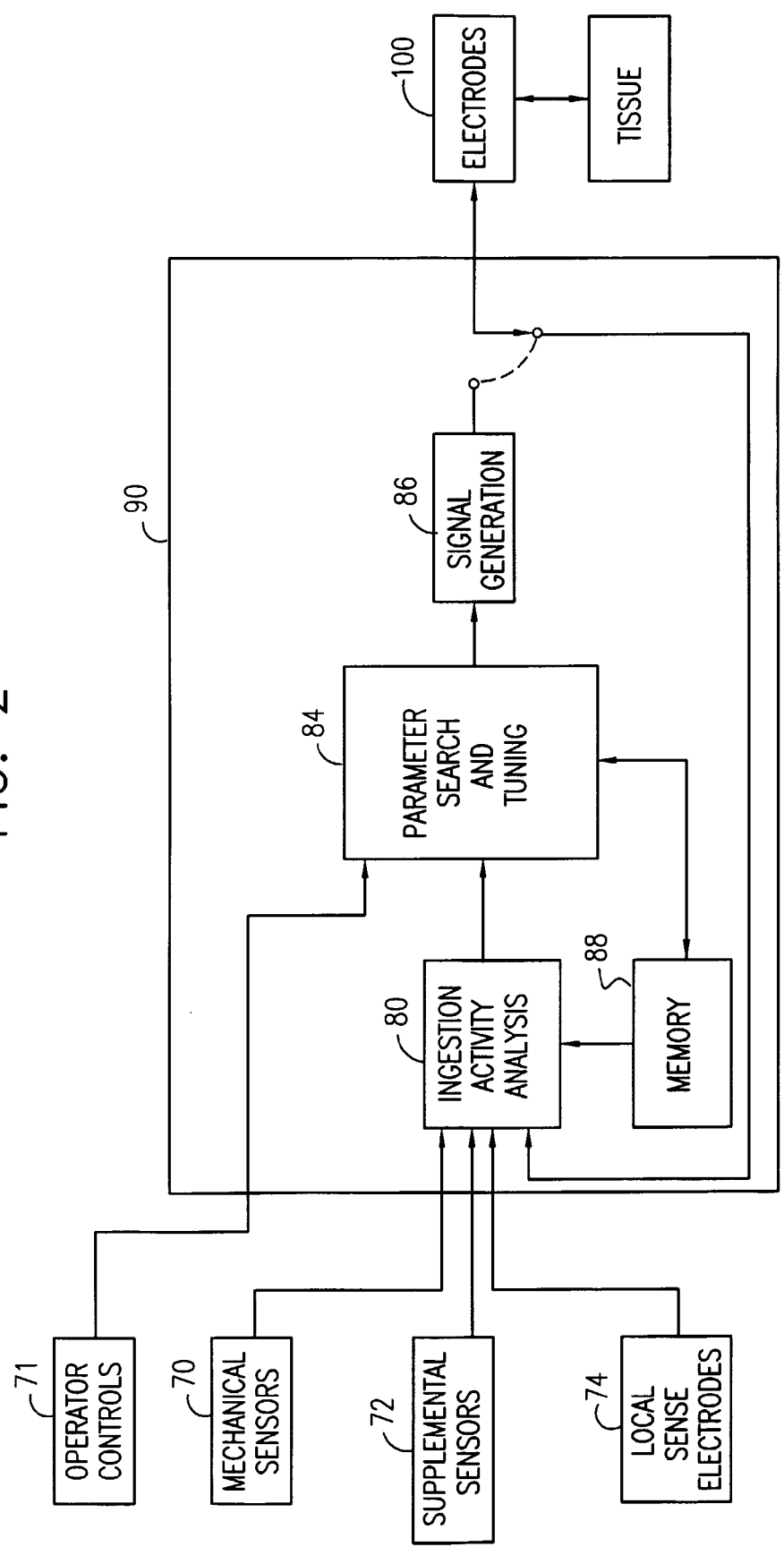
FIG. 2 is a schematic block diagram showing a control unit of the apparatus of FIG. 1, in accordance with a preferred embodiment of the present invention.

FIG. 2 is a schematic block diagram illustrating details of operation of a control unit 90 of apparatus 18, in accordance with a preferred embodiment of the present invention. Preferably, control unit 90 is implanted in patient 10, and receives signals from mechanical sensors 70, supplemental sensors 72, and local sense electrodes 74, all of which are typically implanted on the gastrointestinal tract of the patient or elsewhere on or in the body of the patient. These sensors and electrodes are preferably adapted to provide an "ingestion activity analysis" block 80 of the control unit with information about food ingestion and/or the present state of the stomach.

Preferably, using techniques described hereinbelow, analysis block 80 determines each time that the patient swallows, and also the character and amount of the ingested matter. For example, local sense electrodes 74 coupled to the fundus of the stomach may send signals indicative of fundic electrical activity to analysis block 80, and analysis block 80 identifies aspects of these signals which are characteristic of swallowing of food by the patient. Additionally, mechanical sensors 70 and local sensor electrodes 74 coupled to the corpus and antral regions of the stomach preferably send signals which analysis block 80 identifies as indicative of the onset, duration, and/or intensity of the digestive process in those regions. Preferably, these data are utilized by analysis block 80 to determine a quality of the ingested matter, for example, whether it is predominantly solid or liquid. Alternatively or additionally, these data may be used to determine other characteristics of the ingested material, for example, its nutritional, chemical, and/or caloric content.

In a preferred embodiment, analysis block 80 determines the time delay between swallowing (as measured, preferably, by local sense electrodes 74 on the fundus) and the commencement of electrical and mechanical activity in the antrum. This delay is typically used to differentiate between the ingestion of solid and liquid matter, because solids are generally held in the fundus for at least about 10 minutes before being passed to the antrum, while liquids are generally passed to the antrum essentially immediately.

Alternatively or additionally, the amount of food accumulated in the various regions of stomach 20 is estimated by measuring a level of electrical or mechanical activity in a vicinity of those regions. Further alternatively or additionally, analysis block 80 processes data from supplemental sensors 72 indicative of the blood sugar level of the patient, to enable an evaluation of whether and of what type of food has been ingested.

In order to improve the accuracy of the analyses described hereinabove, analysis block 80 is preferably calibrated by measuring the appropriate electrical response criteria of stomach 20 of patient 10 to various types of solid and liquid food. To ensure appropriate compliance, calibration is preferably performed under the supervision of a healthcare worker.

For some applications, analysis block 80 stores the results of its analysis in a memory block 88 of control unit 90, and these results are later uploaded to an external computer, preferably by a wireless communications link, for review by the patient's physician. Alternatively or additionally, analysis block 80 conveys results of its analysis of the inputs from mechanical sensors 70, supplemental sensors 72, and local sense electrodes 74, to a "parameter search and tuning" block 84 of control unit 90. Block 84 preferably evaluates the analysis performed by analysis block 80 with respect to a pre-programmed or variable ingestion schedule stored in memory block 88, so as to determine whether the patient is eating in compliance with the schedule. Preferably, the schedule can be modified after implantation of control unit 90, by communication from operator controls 71 using methods described hereinbelow. If it is determined that the patient's eating is not in compliance with the schedule (e.g., the patient has eaten too much at one meal, or has eaten too many meals in a day, or has had too much of a certain type of food or drink), then block 84 preferably actuates a signal generator block 86 to generate electrical signals that are applied by current-application electrodes 100 to tissue of patient 10. Block 86 preferably comprises amplifiers, isolation units, and other standard circuitry known in the art of electrical signal generation.

The signals generated by block 86 are preferably configured so as to induce a response appropriate for controlling the patient's eating habits. For example, block 86 may drive current-application electrodes 100 to apply signals to the stomach that induce gastric dysrhythmia and the resultant feeling of discomfort or nausea. Alternatively or additionally, the signals are applied to an aural site of patient 10 (e.g., in a vicinity of the cochlear nerve or the tympanic membrane), and are configured to induce vertigo, or another unpleasant balance-related sensation. Alternatively or additionally, block 86 generates a visual, audio, or other cue to encourage the patient to adhere to the schedule.

For some applications, control unit 90 drives electrodes 100 to apply a modulation signal to muscle in one area of stomach 20, so as to induce a contraction of the stimulated muscle that, in turn, induces satiety when food in an adjacent area of the stomach causes additional stretching of stretch-receptors therein. This signal may be applied in addition to or instead of the signals described hereinabove that produce gastric or other discomfort. The form of contraction-mediated stretching utilized in these applications simulates the normal appetite-reduction action of the stomach's stretch-receptors, without the patient having eaten the quantities of food which would normally be required to trigger this appetite-reduction response. In a preferred application, current-application electrodes 100 are placed around the body of the stomach and are driven to induce a generally steady-state contraction of the corpus, which simulates electrically the squeezing of the corpus produced mechanically by implanted gastric bands known in the art.

Preferably, the signals applied by current-application electrodes 100 include, as appropriate, an Excitable-Tissue Control (ETC) signal and/or an excitatory signal that induces contraction of muscles of the stomach. Aspects of ETC signal application are typically performed in accordance with techniques described in the above-referenced PCT Publications WO 99/03533 and WO 97/25098 and their corresponding US national phase applications Ser. Nos. 09/481,253 and 09/101, 723, mutatis mutandis.

Preferably, evaluation apparatus 18 includes remote operator controls 71, external to the patient's body. This remote unit is typically configured to enable the patient or his physician to change parameters of the ingestion schedule stored in memory block 88. For example, if the patient has lost weight, the physician may change the ingestion schedule to allow a single mid-afternoon snack. Alternatively or additionally, operator controls 71 comprise an override button, so that the patient may eat outside of the designated meal times, or consume a particular food or drink not in accordance with the schedule, if the need arises. Operator controls 71 preferably communicate with control unit 90 using standard methods known in the art, such as magnetic induction or radio frequency signals.

Figure 3:
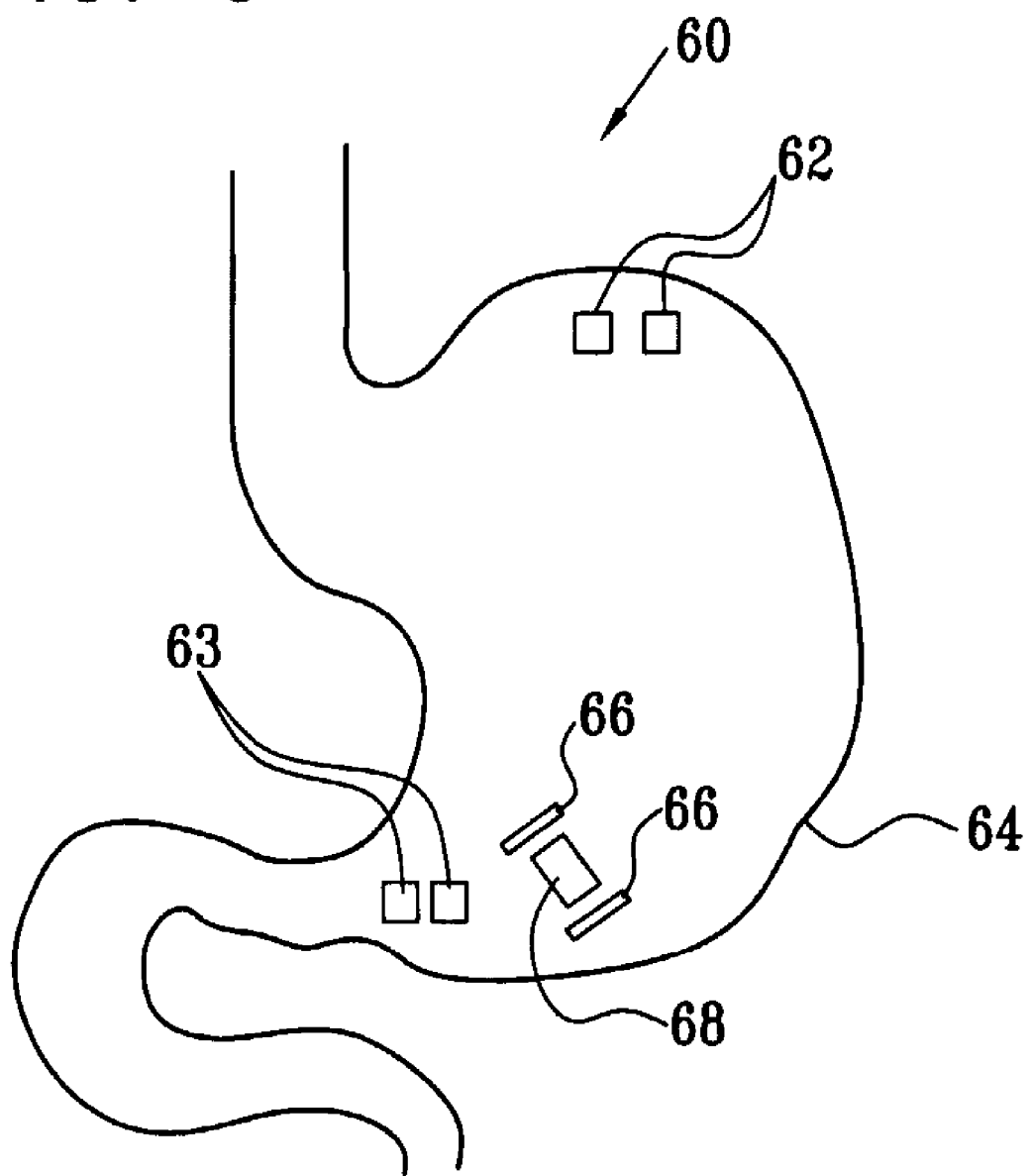
FIG. 3 is a schematic diagram showing experimental apparatus used to measure electrical responses to eating in the stomach of a normal rabbit, in accordance with a preferred embodiment of the present invention.

FIG. 3 is a schematic diagram showing experimental apparatus 60 used to measure electrical responses to eating in the stomach 64 of a normal rabbit, in accordance with a preferred embodiment of the present invention. Bipolar sense electrodes 62 were coupled to the fundus of stomach 64, and bipolar sense electrodes 63 were coupled to the antrum of the stomach. Additionally, two stitch electrodes 66 with a strain gauge 68 located therebetween were coupled to the antrum.

Figure 5A:
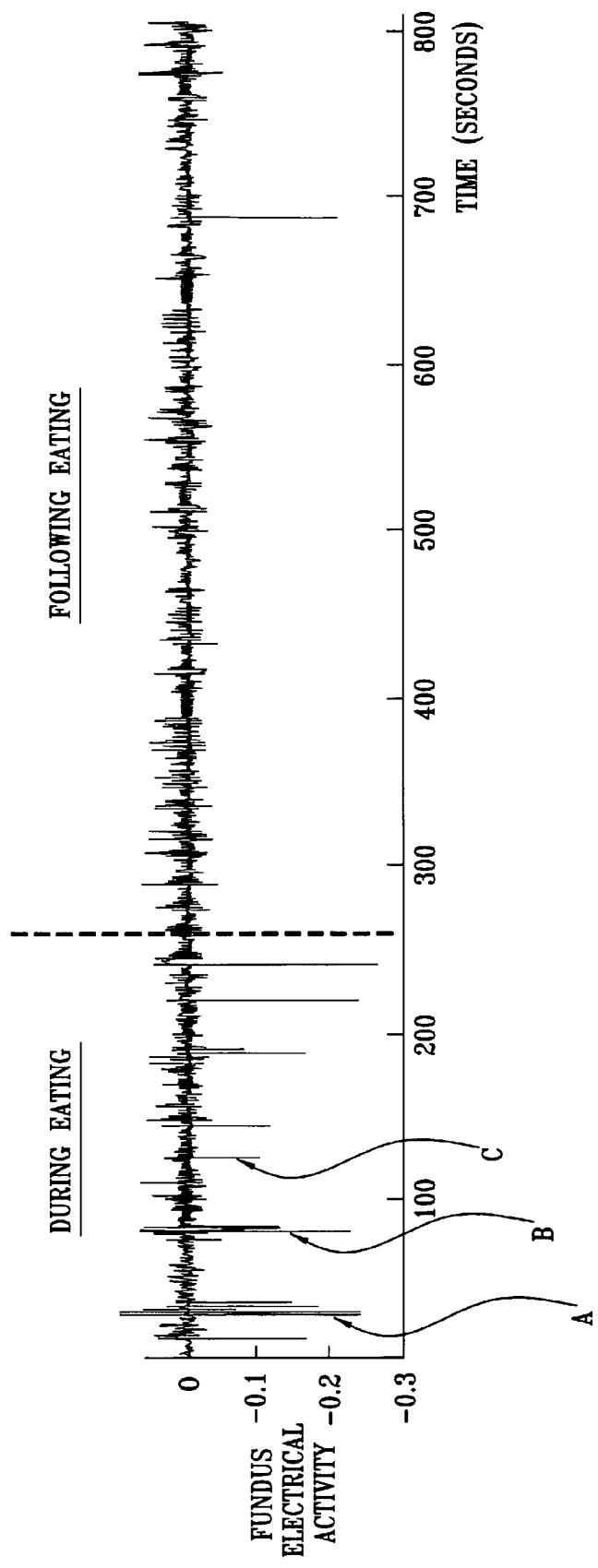
FIGS. 5A is a graph showing electrical activity in the fundus of a normal rabbit during and following eating, and results of analysis thereof, in accordance with a preferred embodiment of the present invention.
Figure 5B:
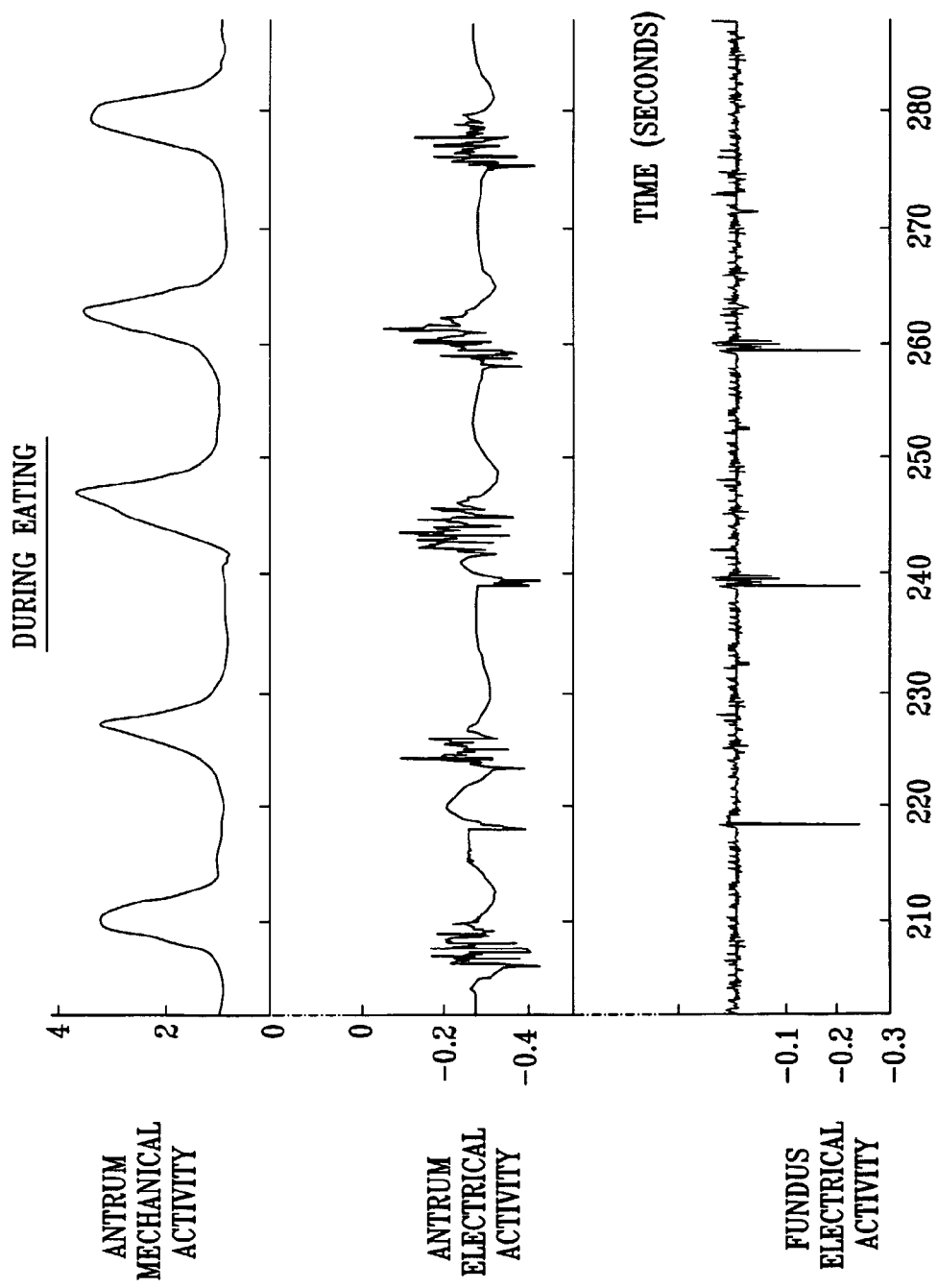
FIG. 5B is a graph showing details of electrical and mechanical activity recorded during the taking of the data shown in FIG. 5A.

Reference is now made to FIGS. 4, 5A and 5B, which are graphs showing the results of experiments performed using apparatus 60 in a rabbit, in accordance with a preferred embodiment of the present invention. FIG. 4 shows electrical activity in the fundus, measured during a five minute period before the rabbit was fed solid food, and during a more than six minute period while the rabbit was eating solid food. It can be seen that the second period is distinguished by markedly increased electrical activity. Spikes, typified by those marked "A," "B," and "C" in this graph, are preferably identified by a control unit operating in accordance with these embodiments of the present invention, and are interpreted as indications of eating. It is noted that in the case of the rabbit experiment shown in FIG. 4, electrical activity as measured by spikes per unit time increased by a factor of about 8, and is therefore considered to be a good indication of the initiation and continuation of eating.

FIG. 5A is a graph showing the electrical response of the fundus of the rabbit stomach, and the results of analysis thereof, in accordance with a preferred embodiment of the present invention. In this experiment, the measurements were first taken for five minutes while the rabbit was eating solid food, and were continued for almost 10 minutes after the rabbit ceased eating. It is clearly seen that the period after the rabbit ate is characterized by significantly less electrical activity than that which occurred during eating. Spikes, such as those marked "A," "B," and "C" in this graph, occur at a rate at least 15 times higher during eating than thereafter, and are therefore preferably used by a control unit to determine both the onset and the termination of eating.

FIG. 5B is an expanded view of some of the data shown in FIG. 5A, additionally showing simultaneous mechanical and electrical activity in the antrum of the rabbit. The top graph shows mechanical activity in the antrum as measured by strain gauge 68 (FIG. 3), and the middle graph shows electrical activity in the antrum, measured by electrodes 63 during the same time period. The repeated co-occurrence of antral mechanical and electrical activity, as seen in FIG. 5B, is indicative of the expected antral mechanical response to antral electrical activity.

The bottom graph of FIG. 5B shows the measured electrical activity in the fundus during the same period, i.e., while the rabbit was eating. It can be seen that, while there is close correlation between mechanical and electrical activity in the antrum, there is no correlation seen between fundic electrical activity and either measure of antral activity. Control unit 90 (FIG. 2) is therefore generally enabled to measure and differentiate between fundic and antral response, and to utilize this information to facilitate the evaluations and determinations described herein.

Figure 6:
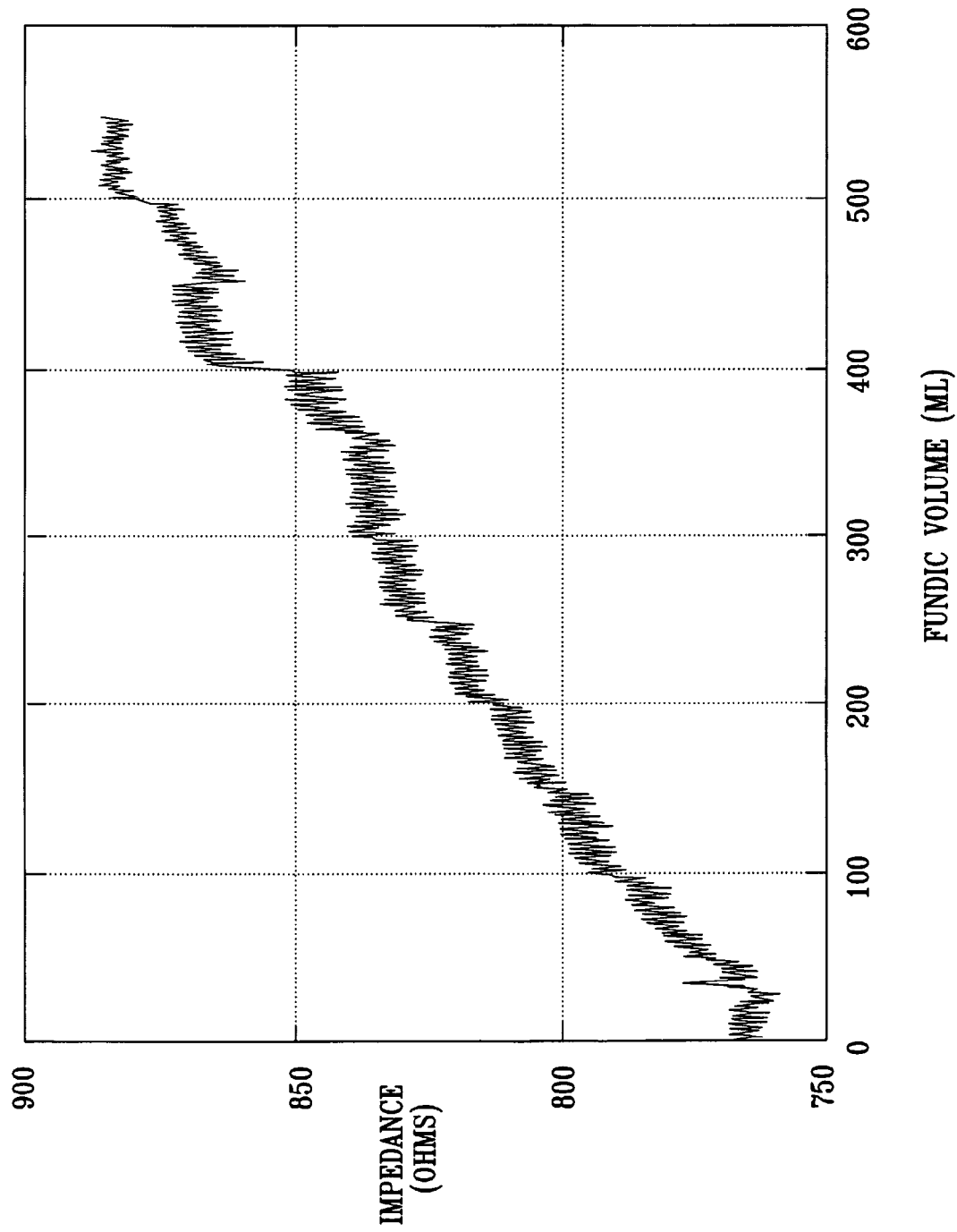
FIG. 6 is a graph showing detail of electrical fundic activity, measured in accordance with a preferred embodiment of the present invention.

FIG. 6 is a graph showing electrical impedance measurements made between two stitch electrodes placed in the stomach of a pig, in accordance with a preferred embodiment of the present invention. In this experiment, fundic volume was measured at the same time as the impedance was measured, and the data show a clear dependence of the impedance on the volume. It is hypothesized that as the fundus distends, the fundic wall thickness decreases, producing a corresponding increase in electrical impedance. Alternatively or additionally, the increased distance between the two electrodes produced as a result of the distension causes the electrical impedance to increase. Similar experimental results (not shown) were obtained when impedance and volume measurements were made in the antrum. Moreover, changes in impedance were found to correlate with waves of antral activity.

Reference is now made to FIGS. 7, 8, 9, and 10, which are graphs showing the results of experiments performed using apparatus (not shown) similar to apparatus 60 in several normal dogs, in accordance with a preferred embodiment of the present invention. All of the dogs fasted for approximately 24 hours prior to eating during the experiments.

Figure 7:
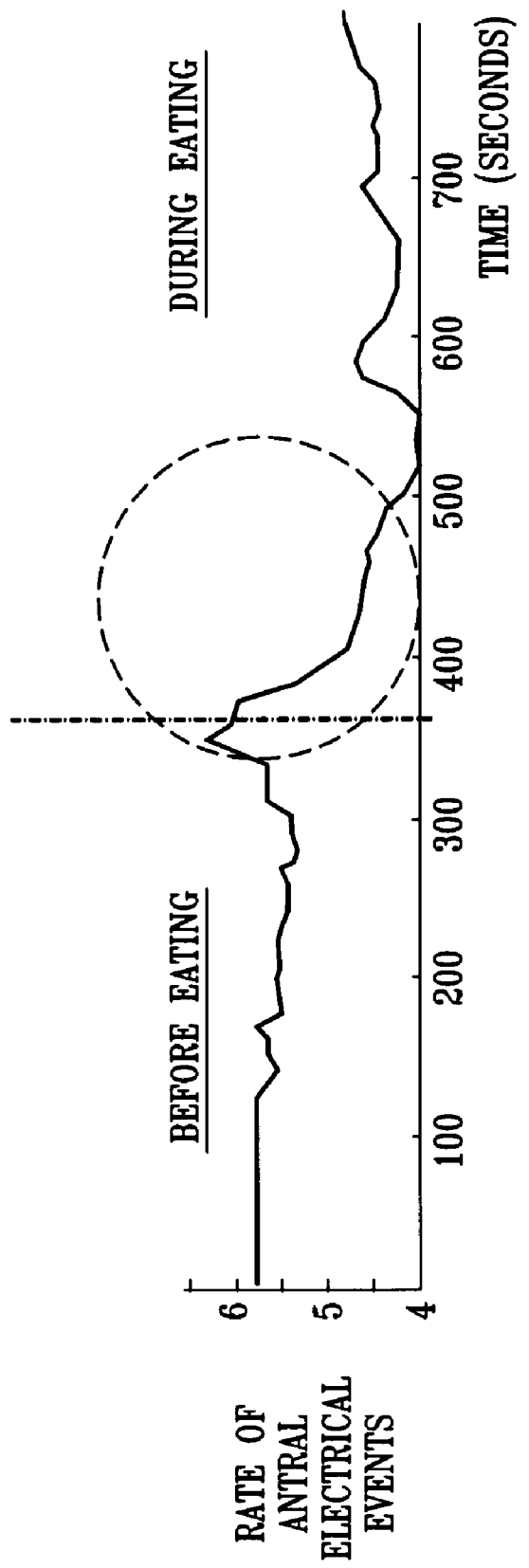
FIG. 7 is a graph showing the rate of electrical events in the antrum of a normal dog before and during eating, and results of analysis thereof, in accordance with a preferred embodiment of the present invention.

FIG. 7 shows the rate of electrical events in the antrum in a dog, measured during a six minute period before the dog was fed solid food and during a more than seven minute period while the dog was eating solid food. Electrical events that were recorded were spikes in the signal of amplitude at least a threshold amount greater than the signal noise. It will be appreciated that detecting changes in other events may be useful for some applications. It will also be appreciated that whereas data shown in the figures reflects measurements of antral electrical events, for some applications the analysis techniques described herein may also be implemented with respect to the rate of fundic electrical events.

It can be seen that the second period is distinguished by a markedly decreased rate of antral electrical events. Such a decrease is preferably identified by a control unit operating in accordance with these embodiments of the present invention, and is interpreted as an indication of eating. It is noted that the rate of antral electrical events, as measured by events per unit time, decreased on average by about 20% beginning about one minute after the initiation of eating, and is therefore considered to be a good indication of the initiation and continuation of eating. (Decreases of up to about 50% were seen in other experiments.) Alternatively or additionally, responsive to a calibration procedure, such a decrease in the rate of antral electrical events may be used to determine other characteristics of the ingested material, for example, its nutritional, chemical, and/or caloric content. Similar results were obtained in experiments on two other dogs (not shown).

Figure 8:
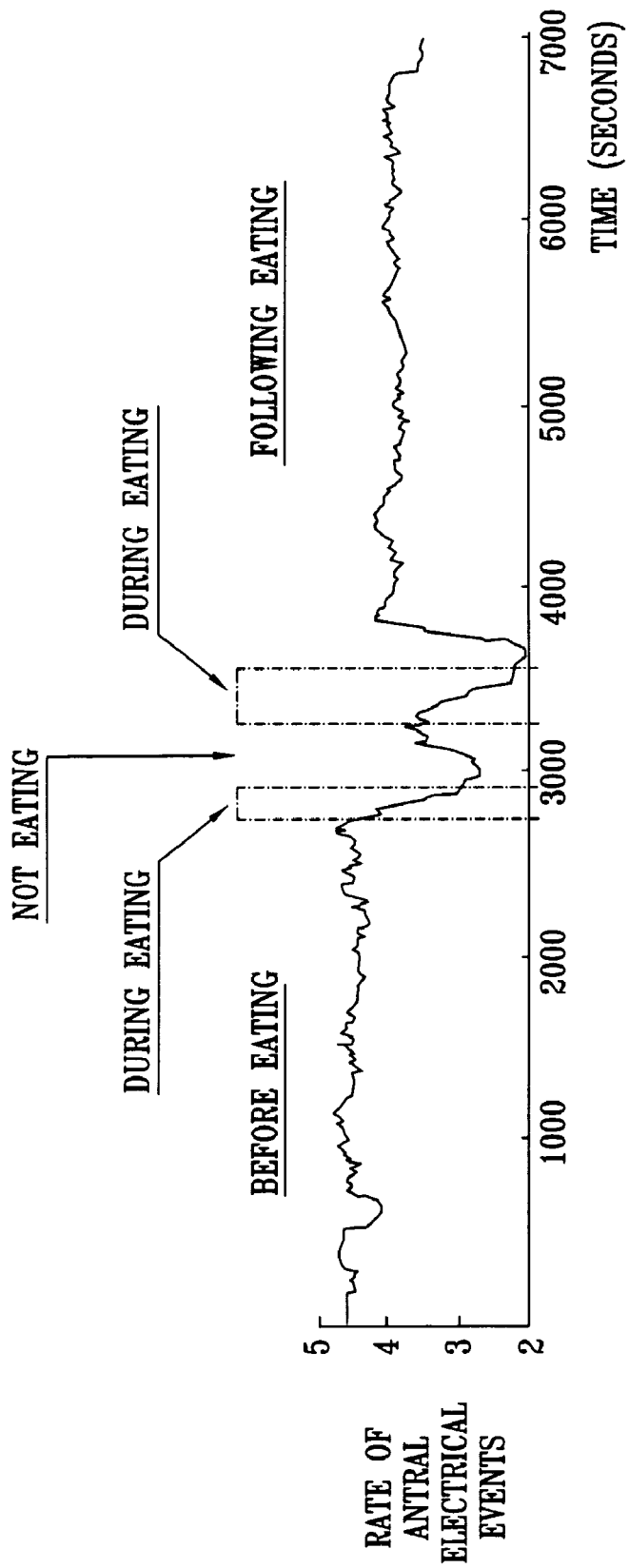
FIG. 8 is a graph showing the rate of electrical events in the antrum of a normal dog before, during, and after eating, and results of analysis thereof, in accordance with a preferred embodiment of the present invention.

FIG. 8 is a graph showing the rate of electrical events in the antrum in a second dog, measured during a more than 40 minute period before the dog was fed solid food, during an approximately 13 minute period while the dog was eating solid food (interrupted by an approximately 6 minute period of non-eating), and during an almost 60 minute period after the dog ceased eating. It is clearly seen that the period beginning approximately four minutes after the dog ceased eating is characterized by return to a rate of antral electrical events almost equal to the rate prior to eating, and significantly higher than the reduced rate during eating. The rate of antral electrical events is therefore preferably used by a control unit to determine both the onset and the termination of antral activity.

Figure 9:
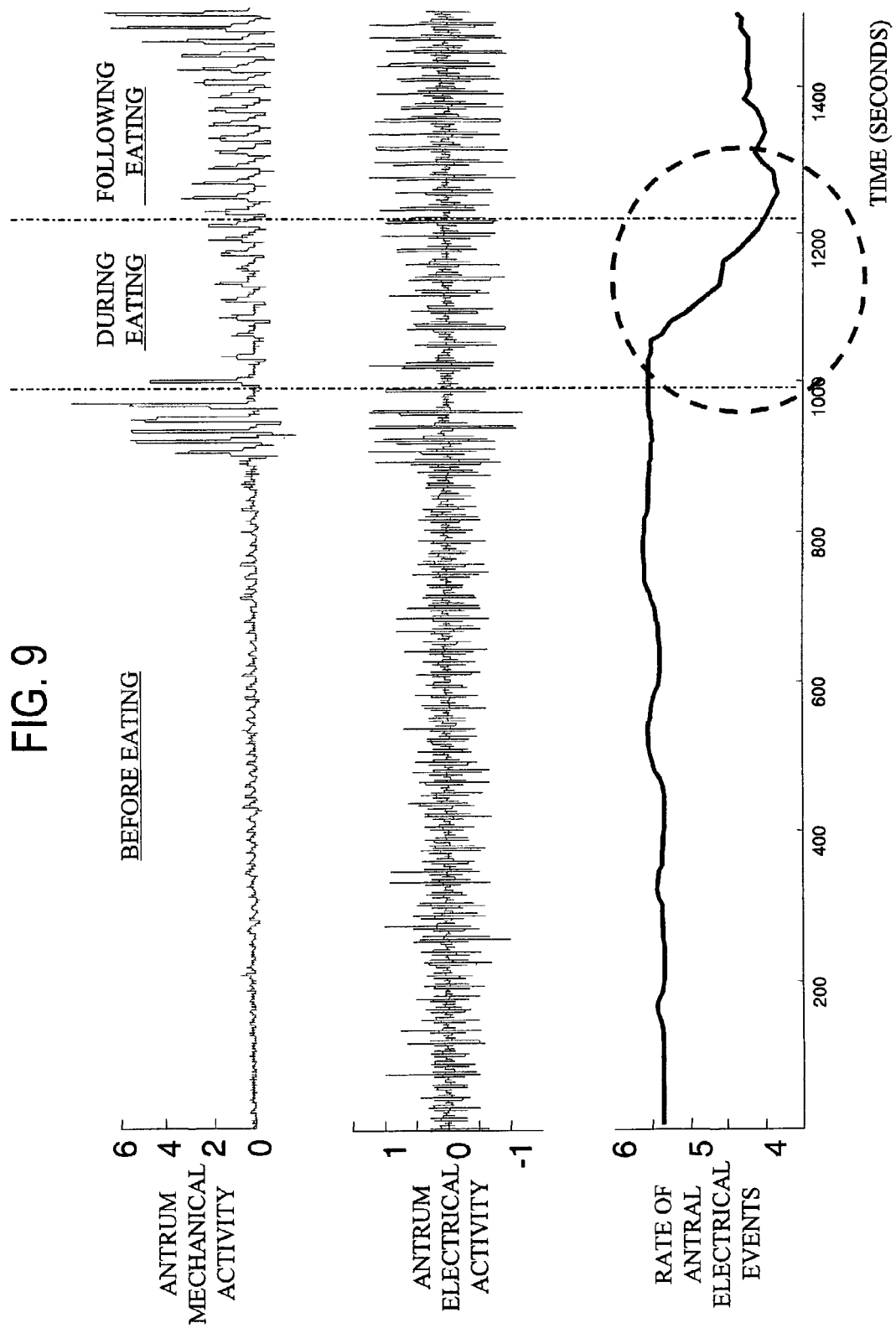
FIG. 9 is a graph showing electrical and mechanical activity and the rate of electrical events in the antrum of a normal dog before, during, and after eating, and results of analysis thereof, in accordance with a preferred embodiment of the present invention.

FIG. 9 is a graph showing simultaneous mechanical activity, electrical activity, and rate of electrical events in the antrum of a third dog, measured during a more than 16 minute period before the dog was fed solid food, during an approximately 3.5 minute period while the dog was eating solid food, and during a more than four minute period after the dog ceased eating. The top graph shows mechanical activity in the antrum as measured by a strain gauge, and the middle graph shows electrical activity in the antrum, measured by electrodes during the same time period. It can be seen that co-occurring mechanical and electrical activity began approximately 1.5 minutes prior to the beginning of eating, corresponding with the onset of cephalic phase activity (brain activity reflecting the mental anticipation of eating).

The bottom graph of FIG. 9 shows the rate of electrical events in the antrum of the dog. It can be seen that the second period is distinguished by a markedly decreased rate of antral electrical events, consistent with the results of the first dog experiment described hereinabove. An increase in mechanical and/or electrical antral activity prior to eating as occurred in this experiment is preferably identified by a control unit operating in accordance with these embodiments of the present invention, and provides additional information that can be interpreted together with information such as the decreased rate of antral electrical events observed in this experiment to provide indications of anticipation of eating, eating and/or gastric digestion.

Figure 10:
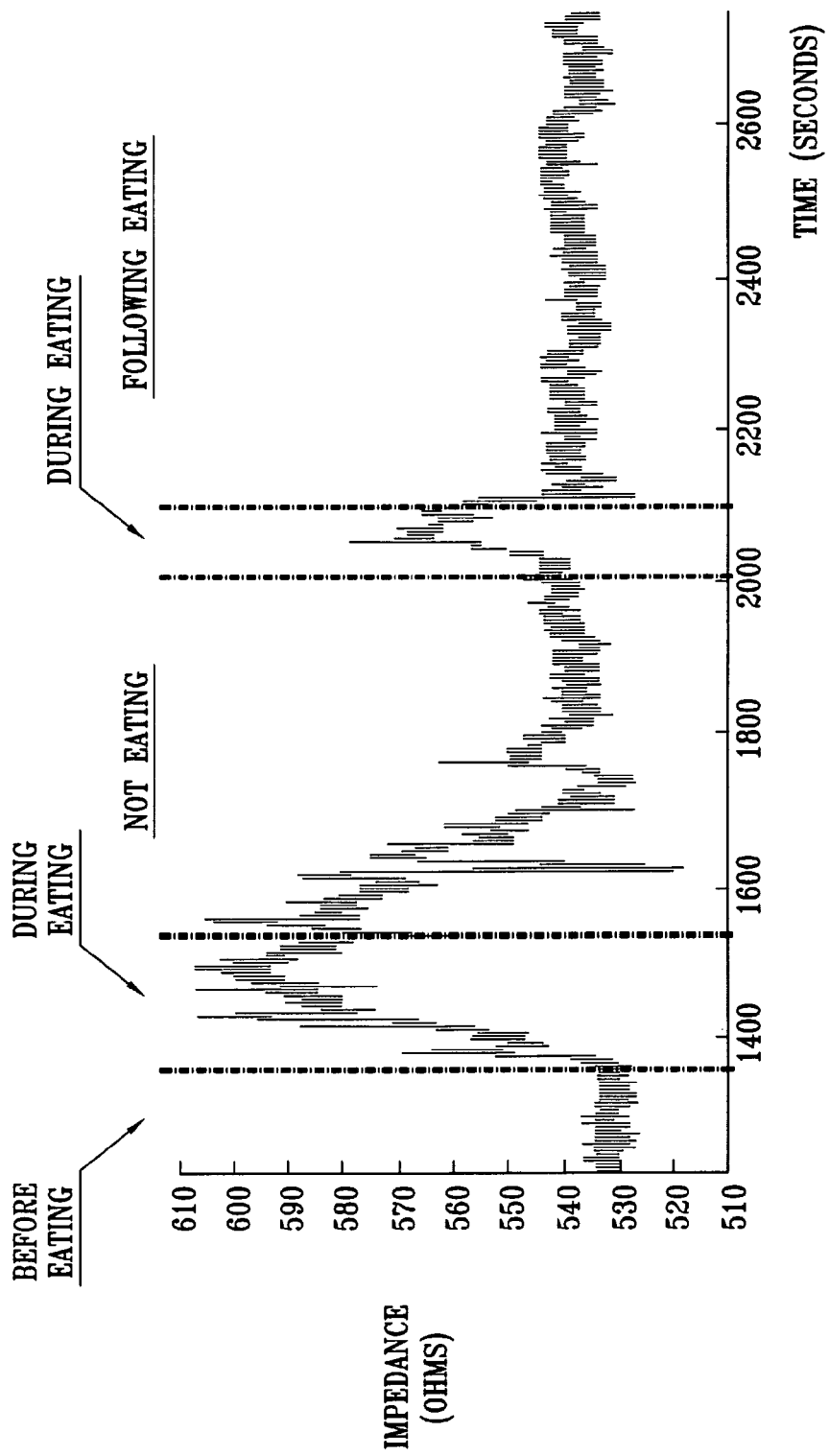
FIG. 10 is a graph showing fundic electrical activity in a normal dog during several periods of eating and non-eating, and results of analysis thereof, in accordance with a preferred embodiment of the present invention.

FIG. 10 is a graph showing electrical impedance measurements made between two stitch electrodes in the fundus of a fourth dog, measured during five sequential periods: (1) an approximately 22 minute period before the dog was fed solid food (portion of period not shown), (2) an approximately three minute period while the dog was eating solid food, (3) an approximately 7.5 minute period during which the dog did not eat, (4) an approximately one minute period while the dog was eating solid food, and (5) a greater than 10 minute period after the dog ceased eating.

It can be seen that the eating periods (second and fourth periods) are distinguished by markedly increased fundic electrical impedance. Such increases are preferably identified by a control unit operating in accordance with these embodiments of the present invention, and are interpreted as indications of eating. This interpretation is supported by the correlation between impedance and volume measurements in the fundus obtained in the pig experiments described hereinabove. It is noted that in the case of the dog experiment shown in FIG. 10, the fundic electrical impedance, as measured in ohms, increased by more than about 12%, beginning less than about one minute after the initiation of eating during the second period, and by about 5% beginning less than about one minute after the initiation of eating during the fourth period. The fundic electrical impedance is therefore considered to be a good indication of the initiation and continuation of eating. Similar results were obtained in two other experiments on different days on the same dog (not shown).

It is clearly seen in FIG. 10 that the period beginning almost immediately after the dog ceased eating (the fifth period) is characterized by a return of fundic electrical impedance to a value almost equal to that prior to eating, and significantly lower than the increased value observed during eating. Fundic electrical impedance is therefore preferably used by a control unit to determine both the onset and the termination of eating.

The inventors have observed that fundic electrical impedance (e.g., as measured in the case of the dog experiment shown in FIG. 10), as an indicator of eating, typically exhibits lower variability than antral electrical impedance, and is less affected by movement and/or change in posture of the subject. Fundic electrical impedance also typically provides more reliable detection of eating than antral activity.

In preferred embodiments of the present invention, measurements of antral and/or fundic electrical impedance are used in conjunction with or separately from other indicators of swallowing or digestion, described hereinabove, in order to track a patient's eating habits. Advantageously, impedance measurements made between two electrodes located even at mutually remote sites on a portion of the stomach can be accurate indicators of global strain of that portion, while a mechanical strain gauge placed at a particular site on the stomach generally only yields an indication of strain at that site.

It will be recognized by persons skilled in the art that more complex combinations of variations in levels of electrical or mechanical activity in different regions of the stomach may occur than those demonstrated in the experiments described hereinabove. For example, certain electrical or mechanical activity may lag the eating of certain amounts and types of food. Examples of more complex combinations (not shown) were obtained in additional experiments in other dogs. Analysis block 80, with proper calibration as described hereinabove, can readily be enabled to evaluate such complex combinations.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A gastric apparatus, comprising:
a set of one or more implantable antral electrodes, configured to be coupled to an antral site of an antrum of a subject and to generate an antral electrode signal responsive to a property of the antrum; and
a control unit, configured to:
receive and analyze the antral electrode signal,
determine a time delay between an onset of eating by the subject and a change in electrical activity in the antrum, the change in electrical activity determined responsive to the antral electrode signal, and
responsively to the delay, determine whether food ingested by the subject is predominantly solid or liquid.

2. An apparatus according to claim 1, wherein the control unit is adapted to determine, responsive to the time delay, an extent to which the ingested food includes solid food matter.

3. An apparatus according to claim 1, further comprising a set of one or more implantable fundic electrodes, configured to be coupled to a fundic site of a fundus of a stomach of the subject, and wherein the control unit is configured to identify the onset of eating using the set of fundic electrodes.

4. An apparatus according to claim 3, wherein the control unit is configured to identify, as indicative of the onset of eating, an increase in an amplitude of an electrical potential change generated responsive to a contraction of a muscle of the fundus, detected using the set of fundic electrodes.

5. An apparatus according to claim 1, wherein the change in the electrical activity in the antrum is an onset of a decreased rate of electrical events in the antrum, and wherein the control unit is configured to determine the time delay between the onset of eating and the onset of the decreased rate of the electrical events in the antrum.

6. An apparatus according to claim 5, wherein the control unit is configured to determine, responsive to the time delay, an extent to which the ingested food includes solid food matter.

7. An apparatus according to claim 5, wherein the control unit is configured to determine, responsive to the time delay, an extent to which the ingested food includes liquid food matter.

8. An apparatus according to claim 1, wherein the change in the electrical activity in the antrum is an onset of increased electrical activity in the antrum, and wherein the control unit is configured to determine the time delay between the onset of eating and the onset of the increased electrical activity in the antrum.

9. An apparatus according to claim 8, wherein the control unit is configured to determine, responsive to the time delay, an extent to which the ingested food includes solid food matter.

10. An apparatus according to claim 8, wherein the control unit is configured to determine, responsive to the time delay, an extent to which the ingested food includes liquid food matter.

11. An apparatus according to claim 1, and comprising a set of one or more current-application electrodes, configured to be coupled to a tissue of the subject, and wherein the control unit is configured to drive an Excitable-Tissue Control (ETC) signal to the tissue, responsive to the analysis, through the set of current-application electrodes into the tissue.

12. An apparatus according to claim 1, further comprising a set of one or more current-application electrodes, configured to be coupled to a tissue of the subject, wherein the control unit is configured to drive a current through the set of current-application electrodes into the tissue.

13. An apparatus according to claim 12, wherein the set of current-application electrodes is configured to be applied to a stomach of the subject.

14. An apparatus according to claim 13, wherein the control unit is configured to configure the current to induce a sensation selected from the group consisting of: a sensation of discomfort, and a sensation of nausea.

15. An apparatus according to claim 12, wherein the set of current-application electrodes is configured to be applied to an esophageal site of the subject.

16. An apparatus according to claim 1, further comprising a signal generator, wherein the control unit is configured to actuate the signal generator to convey an ingestion-control signal to the subject.

17. An apparatus according to claim 1, wherein the apparatus is configured to treat obesity of the subject.

18. An apparatus according to claim 1, wherein the change in the electrical activity in the antrum is an onset of the electrical activity, and wherein the control unit is configured to determine the time delay between the onset of eating and the onset of the electrical activity.

19. An apparatus according to claim 1, further comprising at least one sensor, configured to placed at a site selected from the group consisting of: a site on an esophagus and a site on a throat, and to generate a signal indicative of swallowing, and wherein the control unit is configured to identify the onset of eating responsively to the signal.

20. A gastric apparatus, comprising:
a gastric sensor, configured to be coupled to a gastric site of a subject and to generate a gastric sensor signal responsive to a property of the gastric site and
a control unit, configured to receive and analyze the gastric sensor signal, and to determine, responsive thereto, a characteristic of a food ingested by the subject, the characteristic selected from the group consisting of: whether the food is predominantly solid or liquid, and a caloric content of the food,
wherein the gastric sensor comprises a set of one or more fundic electrodes, configured to generate a fundic electrode signal responsive to a property of the fundus, and wherein the control unit is configured to receive and analyze the fundic electrode signal, and to determine, responsive thereto, the characteristic of the ingested food, and
wherein the fundic electrode set is configured to generate the fundic electrode signal responsive to an electrical potential change generated responsive to a contraction of a muscle of the fundus.

21. An apparatus according to claim 20, wherein the control unit is configured to determine, responsive to a parameter of the fundic electrode signal, the characteristic of the ingested food, the parameter selected from the group consisting of: an amplitude of the fundic electrode signal, a duration of the fundic electrode signal, and a change in rate of fundic electrode signal events.

22. An apparatus according to claim 20, wherein the control unit is configured to determine, responsive to a frequency of the fundic electrode signal, the characteristic of the ingested food.

23. An apparatus according to claim 20, wherein the control unit is configured to identify an increase in an amplitude of the fundic electrode signal as indicative of an event selected from the group consisting of: eating and an onset of eating.

24. An apparatus according to claim 20, wherein the control unit is configured to identify an increase in a frequency of the fundic electrode signal as indicative of an event selected from the group consisting of: eating and an onset of eating.

25. An apparatus according to claim 24, wherein the control unit is configured to detect the onset of the selected event, responsive to the increase in the frequency being greater than about 10 percent.

26. An apparatus according to claim 20, wherein the control unit is configured to identify a substantial return towards a baseline value of a parameter of the fundic electrode signal as indicative of a termination of eating, the parameter selected from the group consisting of: an amplitude of the fundic electrode signal, and a frequency of the fundic electrode signal.

27. A method comprising:
coupling a gastric sensor to a gastric site of the subject, and sensing a property of the gastric site using the gastric sensor;
analyzing the property of the gastric site; and
determining, responsive to the analysis, a characteristic of a food ingested by the subject, the characteristic selected from the group consisting of: whether the food is predominantly solid or liquid, and a caloric content of the food,
wherein the gastric site includes an antral site, and wherein sensing the property comprises sensing a property of an antrum of a stomach.

28. A method according to claim 27, wherein sensing the property of the antrum comprises sensing an electrical property of the antrum.

29. A method according to claim 28, wherein determining the characteristic of the food comprises:
determining a time delay between an onset of eating by the subject and a change in electrical activity in the antrum; and
responsively to the delay, determining whether food ingested by the subject is predominantly solid or liquid.

30. A method according to claim 29, wherein determining whether the ingested food is solid or liquid comprises determining, responsive to the time delay, an extent to which the ingested food includes solid food matter.

31. A method according to claim 29, wherein the change in the electrical activity in the antrum is an onset of a decreased rate of electrical events in the antrum, and wherein determining the time delay comprises determining the time delay between the onset of eating and the onset of the decreased rate of the electrical events in the antrum.

32. A method according to claim 29, wherein the change in the electrical activity in the antrum is an onset of increased electrical activity in the antrum, and wherein determining the time delay comprises determining the time delay between the onset of eating and the onset of the increased electrical activity in the antrum.

33. A method according to claim 29, wherein determining the time delay comprises coupling a set of one or more implantable fundic electrodes to a fundic site of a fundus of a stomach of the subject, and identifying the onset of eating using the fundic electrodes.

34. A method according to claim 33, wherein identifying comprises identifying an increase in an amplitude of an electrical potential change generated responsive to a contraction of a muscle of the fundus, detected using the fundic electrodes.

35. A method according to claim 29, wherein determining the time delay comprises placing at least one sensor at a site selected from the group consisting of: a site on an esophagus and a site on a throat, using the sensor to generate a signal indicative of swallowing, and identifying the onset of eating responsively to the signal.

36. A method according to claim 27, and comprising driving a current into tissue of the subject responsive to the analysis.

37. A method according to claim 36, wherein driving the current comprises driving the current into a stomach of the subject.

38. A method according to claim 37, wherein driving the current comprises configuring the current to induce a sensation selected from the group consisting of: a sensation of discomfort, and a sensation of nausea.

39. A method according to claim 36, wherein driving the current comprises applying an Excitable-Tissue Control (ETC) signal to the tissue.

40. An apparatus according to claim 36, wherein driving the current comprises driving the current into an esophageal site of the subject.

41. A method according to claim 27, further comprising conveying an ingestion-control signal to the subject responsive to the analysis.

42. A method according to claim 37, further comprising treating obesity of the subject responsive to the analysis.

43. A method comprising:
coupling a gastric sensor to a gastric site of the subject, and sensing a property of the gastric site using the gastric sensor;
analyzing the property of the gastric site and
determining, responsive to the analysis, a characteristic of a food ingested by the subject, the characteristic selected from the group consisting of: whether the food is predominantly solid or liquid, and a caloric content of the food,
wherein the gastric site includes a fundic site, and wherein sensing the property comprises sensing a property of a fundus of a stomach.

44. A method according to claim 43, wherein sensing the property of the fundus comprises sensing an electrical property of the fundus.

45. A method according to claim 44, wherein the fundic site includes two fundic sites, and wherein sensing the electrical property comprises sensing a measure of electrical impedance between the two fundic sites.

46. A method according to claim 44, wherein sensing the property comprises sensing an electrical potential change generated responsive to a contraction of a muscle of the fundus.

47. A gastric apparatus, comprising:
a gastric sensor, configured to be coupled to a gastric site of a subject and to generate a gastric sensor signal responsive to a property of the gastric site; and
a control unit, configured to receive and analyze the gastric sensor signal, and to determine, responsive thereto, a caloric content of the food.

48. An apparatus according to claim 47, wherein the gastric sensor comprises a set of one or more implantable antral electrodes, configured to be coupled to an antral site of an antrum of a stomach of the subject and to generate an antral electrode signal responsive to a property of the antrum, and wherein the control unit is configured to receive and analyze the antral electrode signal, and to determine, responsive thereto, the caloric content of the ingested food.

49. A gastric apparatus, comprising:
a gastric sensor, configured to be coupled to a gastric site of a subject and to generate a gastric sensor signal responsive to a property of the gastric site
a set of one or more current-application electrodes, configured to be coupled to a tissue of a stomach of the subject; and
a control unit, configured to:
receive and analyze the gastric sensor signal,
determine, responsive thereto, a characteristic of a food ingested by the subject, the characteristic selected from the group consisting of: whether the food is predominantly solid or liquid, and a caloric content of the food,
responsive to the analysis, drive a current through the set of current-application electrodes into the tissue, and
configure the current to induce a feeling of satiation by performing an action selected from the group consisting of: configuring the current to induce contraction of stomach muscles, and configuring the current to enhance mobility of chyme in the stomach.

50. An apparatus according to claim 49, wherein the gastric sensor comprises a set of one or more fundic sensors, configured to be coupled to a fundic site of a fundus of a stomach of the subject and to generate a fundic sensor signal responsive to a property of the fundus, and wherein the control unit is configured to receive and analyze the fundic sensor signal, and to determine, responsive thereto, the characteristic of the ingested food.

51. An apparatus according to claim 50, wherein the fundic sensor set comprises a set of one or more fundic electrodes, and wherein the control unit is configured to determine, the characteristic of the ingested food using the fundic electrodes.

52. An apparatus according to claim 51, wherein the fundic electrode set comprises two fundic electrodes, configured to be coupled to two sites of the fundus, and wherein the control unit is configured to identify a measure of electrical impedance between the two sites of the fundus.

53. An apparatus according to claim 52, wherein the control unit is configured to determine the characteristic of the ingested food, responsive to a change in the measure of electrical impedance.

54. An apparatus according to claim 49, wherein the gastric sensor comprises a set of one or more implantable antral sensors, configured to be coupled to an antral site of an antrum of a stomach of the subject and to generate an antral sensor signal responsive to a property of the antrum, and wherein the control unit is configured to receive and analyze the antral sensor signal, and to determine, responsive thereto, the characteristic of the ingested food.

55. An apparatus according to claim 54, wherein the antral sensor set comprises a set of implantable antral electrodes, configured to generate an antral electrode signal responsive to a property of the antrum, and wherein the control unit is configured to receive and analyze the antral electrode signal, and to determine, responsive thereto, the characteristic of the ingested food.

56. An apparatus according to claim 55, wherein the control unit is configured to determine, responsive to a parameter of the antral electrode signal, the characteristic of the ingested food, the parameter selected from the group consisting of: an amplitude of the antral electrode signal, a duration of the antral electrode signal, and a change in a rate of antral electrode signal events.

57. An apparatus according to claim 55, wherein the control unit is configured to determine, responsive to a frequency of the antral electrode signal, the characteristic of the ingested food.

58. An apparatus according to claim 55, wherein the control unit is configured to determine, responsive to a spike energy per antral cycle of electrical activity, the characteristic of the ingested food.

59. An apparatus according to claim 49, wherein the control unit is configured to configure the current to induce the contraction of the stomach muscles in order to induce the feeling of satiation.

60. An apparatus according to claim 59, wherein the control unit is configured to configure the current to induce a generally steady-state contraction of a corpus of the stomach.

61. An apparatus according to claim 49, wherein the control unit is configured to configure the current to enhance the mobility of the chyme in the stomach in order to induce the feeling of satiation.

62. A method comprising:
coupling a gastric sensor to a gastric site of the subject, and sensing a property of the gastric site using the gastric sensor;
analyzing the property of the gastric site and
determining, responsive to the analysis, a caloric content of the food.

63. A method according to claim 62, wherein the gastric site includes an antral site, and wherein sensing the property comprises sensing an electrical property of an antrum of a stomach.

64. A method comprising:
coupling a gastric sensor to a gastric site of the subject, and sensing a property of the gastric site using the gastric sensor;
analyzing the property of the gastric site;
determining, responsive to the analysis, a characteristic of a food ingested by the subject, the characteristic selected from the group consisting of: whether the food is predominantly solid or liquid, and a caloric content of the food;
driving a current into tissue of a stomach of the subject responsive to the analysis; and
configuring the current to induce a feeling of satiation, by performing an action selected from the group consisting of: configuring the current to induce contraction of stomach muscles, and configuring the current to enhance mobility of chyme in the stomach.

65. A method according to claim 64, wherein configuring the current comprises configuring the current to induce the contraction of the stomach muscles in order to induce the feeling of satiation.

66. A method according to claim 65, wherein configuring the current comprises configuring the current to induce a generally steady-state contraction of a corpus of the stomach.

67. A method according to claim 64, wherein configuring the current comprises configuring the current to enhance the mobility of the chyme in the stomach in order to induce the feeling of satiation.

* * * * *